(12) United States Patent
Ochranek et al.

(10) Patent No.: US 12,007,403 B2
(45) Date of Patent: Jun. 11, 2024

(54) AUTOMATED DIAGNOSTIC ANALYZERS HAVING REAR ACCESSIBLE TRACK SYSTEMS AND RELATED METHODS

(71) Applicants: Abbott Laboratories, Abbott Park, IL (US); Canon Medical Systems Corporation, Otawara (JP)

(72) Inventors: Brian L. Ochranek, Abbott Park, IL (US); David C. Arnquist, Abbott Park, IL (US); Takehiko Oonuma, Otawara (JP); Hirotoshi Tahara, Otawara (JP); Naoto Sato, Otawara (JP); Bradley P. Smith, Abbott Park, IL (US)

(73) Assignees: Abbott Laboratories, Abbott Park, IL (US); Canon Medical Systems Corporation, Otawara (JP)

(*) Notice: Subject to any disclaimer, the term of this patent is extended or adjusted under 35 U.S.C. 154(b) by 79 days.

(21) Appl. No.: 17/479,575

(22) Filed: Sep. 20, 2021

(65) Prior Publication Data
US 2022/0011335 A1  Jan. 13, 2022

Related U.S. Application Data

(63) Continuation of application No. 16/357,972, filed on Mar. 19, 2019, now Pat. No. 11,125,766, which is a
(Continued)

(51) Int. Cl.
*G01N 35/04* (2006.01)
*G01N 33/53* (2006.01)
(Continued)

(52) U.S. Cl.
CPC ......... *G01N 35/04* (2013.01); *G01N 33/5302* (2013.01); *G01N 35/00732* (2013.01);
(Continued)

(58) Field of Classification Search
CPC ............... G01N 35/04; G01N 33/5302; G01N 35/00732; G01N 35/025; G01N 35/10;
(Continued)

(56) References Cited

U.S. PATENT DOCUMENTS 3,449,959 A   6/1969  Grimshaw
3,451,433 A   6/1969  Cunningham et al.
(Continued)

FOREIGN PATENT DOCUMENTS

CN   100448969   1/2009
CN   101470125   7/2009
(Continued)

OTHER PUBLICATIONS

National Intellectual Property Administration, P.R. China, "First Office Action", issued in connection with Chinese Patent Application No. 201710834908.6 dated Mar. 10, 2020, translation included, 22 pages.
(Continued)

*Primary Examiner* — Christine T Mui
(74) *Attorney, Agent, or Firm* — Hanley, Flight & Zimmerman, LLC

(57) ABSTRACT

Example apparatus and methods related to automated diagnostic analyzers having rear accessible track systems are described herein. An example apparatus disclosed herein includes an analyzer to perform a diagnostic test. The analyzer has a first side and a second side opposite the first side. The example apparatus includes a loading bay disposed on the first side of the analyzer to receive a first carrier and a pipetting mechanism coupled to the analyzer adjacent the second side. The example apparatus also includes a first carrier shuttle to transport the first carrier from a first location adjacent the loading bay to a second location adjacent the pipetting mechanism and a track disposed
(Continued)

adjacent the second side of the analyzer to transfer a second carrier to a third location adjacent the pipetting mechanism.

21 Claims, 6 Drawing Sheets

Related U.S. Application Data continuation of application No. 15/099,000, filed on Apr. 14, 2016, now Pat. No. 10,267,818, which is a continuation of application No. 14/213,048, filed on Mar. 14, 2014, now Pat. No. 9,335,338.

(60) Provisional application No. 61/794,311, filed on Mar. 15, 2013.

(51) Int. Cl.
*G01N 35/00* (2006.01)
*G01N 35/02* (2006.01)
*G01N 35/10* (2006.01)

(52) U.S. Cl.
CPC ............ *G01N 35/025* (2013.01); *G01N 35/10* (2013.01); *G01N 35/02* (2013.01); *G01N 2035/0406* (2013.01); *Y10T 436/11* (2015.01); *Y10T 436/113332* (2015.01)

(58) Field of Classification Search
CPC ............ G01N 35/02; G01N 2035/0406; Y10T 436/11; Y10T 436/113332
USPC ......................................................... 422/64
See application file for complete search history.

(56) References Cited

U.S. PATENT DOCUMENTS

| | | |
|---|---|---|
| 3,484,206 A | 12/1969 | Loebl |
| 4,095,077 A | 6/1978 | Schneider et al. |
| 4,319,996 A | 3/1982 | Vincent et al. |
| 4,335,693 A | 6/1982 | Cowles |
| 4,390,391 A | 6/1983 | Fujita et al. |
| 4,515,752 A | 5/1985 | Miramanda |
| 4,608,472 A | 8/1986 | Kato |
| 4,738,825 A | 4/1988 | Kelln et al. |
| 4,743,423 A | 5/1988 | Turner et al. |
| 4,756,877 A | 7/1988 | Veronesi et al. |
| 4,774,055 A | 9/1988 | Wakatake et al. |
| 4,808,380 A | 2/1989 | Minekane |
| 4,848,917 A | 7/1989 | Benin et al. |
| 4,849,177 A | 7/1989 | Jordan |
| 4,906,433 A | 3/1990 | Minekane |
| 5,037,612 A | 8/1991 | Takahashi et al. |
| 5,051,238 A | 9/1991 | Umetsu et al. |
| 5,071,625 A | 12/1991 | Kelln et al. |
| 5,077,013 A | 12/1991 | Guigan |
| 5,154,896 A | 10/1992 | Mochida et al. |
| 5,171,538 A | 12/1992 | Tremmel |
| 5,244,633 A | 9/1993 | Jakubowicz et al. |
| 5,250,440 A | 10/1993 | Kelln et al. |
| 5,266,268 A | 11/1993 | Antocci et al. |
| 5,270,212 A | 12/1993 | Horiuchi et al. |
| 5,311,426 A | 5/1994 | Donohue et al. |
| 5,314,825 A | 5/1994 | Weyrauch et al. |
| 5,352,612 A | 10/1994 | Huber et al. |
| 5,358,691 A | 10/1994 | Clark et al. |
| 5,360,597 A | 11/1994 | Jakubowicz et al. |
| 5,419,871 A | 5/1995 | Muszak et al. |
| 5,422,271 A | 6/1995 | Chen et al. |
| 5,424,036 A | 6/1995 | Ushikubo |
| 5,424,212 A | 6/1995 | Pinsl-Ober et al. |
| 5,434,083 A | 7/1995 | Mitsumaki et al. |
| 5,439,646 A | 8/1995 | Tanimizu et al. |
| 5,443,791 A | 8/1995 | Cathcart et al. |
| 5,444,152 A | 8/1995 | Ishikawa et al. |
| 5,445,794 A | 8/1995 | Wihlborg |
| 5,447,687 A | 9/1995 | Lewis et al. |
| 5,455,175 A | 10/1995 | Wittwer et al. |
| 5,460,780 A | 10/1995 | Devaney, Jr. et al. |
| 5,460,968 A | 10/1995 | Yoshida et al. |
| 5,462,715 A | 10/1995 | Koch et al. |
| 5,466,574 A | 11/1995 | Liberti et al. |
| 5,470,744 A | 11/1995 | Astle |
| 5,482,834 A | 1/1996 | Gillespie |
| 5,482,839 A | 1/1996 | Ashihara et al. |
| 5,482,861 A | 1/1996 | Clark et al. |
| 5,494,170 A | 2/1996 | Burns |
| 5,518,693 A | 5/1996 | Tomasso et al. |
| 5,525,300 A | 6/1996 | Danssaert et al. |
| 5,527,673 A | 6/1996 | Reinhartz et al. |
| 5,536,475 A | 7/1996 | Moubayed et al. |
| 5,536,481 A | 7/1996 | Mabire et al. |
| 5,538,381 A | 7/1996 | Erbes |
| 5,538,849 A | 7/1996 | Uematsu et al. |
| 5,538,976 A | 7/1996 | Okada et al. |
| 5,548,826 A | 8/1996 | Sayers |
| 5,558,839 A | 9/1996 | Matte et al. |
| 5,559,002 A | 9/1996 | Uzan et al. |
| 5,567,595 A | 10/1996 | Kok |
| 5,571,325 A | 11/1996 | Ueyama et al. |
| 5,571,481 A | 11/1996 | Powell et al. |
| 5,575,976 A | 11/1996 | Choperena et al. |
| 5,576,215 A | 11/1996 | Burns et al. |
| 5,578,269 A | 11/1996 | Yaremko et al. |
| 5,578,270 A | 11/1996 | Reichler et al. |
| 5,580,524 A | 12/1996 | Forrest et al. |
| 5,582,796 A | 12/1996 | Carey et al. |
| 5,585,068 A | 12/1996 | Panetz et al. |
| 5,587,129 A | 12/1996 | Kurosaki et al. |
| 5,589,137 A | 12/1996 | Markin et al. |
| 5,595,707 A | 1/1997 | Copeland et al. |
| 5,599,501 A | 2/1997 | Carey et al. |
| 5,609,822 A | 3/1997 | Carey et al. |
| 5,610,073 A | 3/1997 | Chu et al. |
| 5,611,994 A | 3/1997 | Bailey et al. |
| 5,620,898 A | 4/1997 | Yaremko et al. |
| 5,621,778 A | 4/1997 | Erbes |
| 5,632,399 A | 5/1997 | Palmieri et al. |
| 5,637,275 A | 6/1997 | Carey et al. |
| 5,639,425 A | 6/1997 | Komiyama et al. |
| 5,641,006 A | 6/1997 | Autrey |
| 5,650,327 A | 7/1997 | Copeland et al. |
| 5,653,940 A | 8/1997 | Carey et al. |
| 5,654,199 A | 8/1997 | Copeland et al. |
| 5,654,200 A | 8/1997 | Copeland et al. |
| 5,656,493 A | 8/1997 | Mullis et al. |
| 5,658,532 A | 8/1997 | Kurosaki et al. |
| 5,658,799 A | 8/1997 | Choperena et al. |
| 5,670,114 A | 9/1997 | Sakazume et al. |
| 5,670,120 A | 9/1997 | Degenhardt et al. |
| 5,670,375 A | 9/1997 | Seaton et al. |
| 5,677,188 A | 10/1997 | Mitsumaki et al. |
| 5,679,309 A | 10/1997 | Bell |
| 5,681,530 A | 10/1997 | Kuster et al. |
| 5,682,026 A | 10/1997 | Auclair et al. |
| 5,686,046 A | 11/1997 | Malek et al. |
| 5,693,292 A | 12/1997 | Choperena et al. |
| 5,698,450 A | 12/1997 | Ringrose et al. |
| 5,702,019 A | 12/1997 | Grimard |
| 5,702,950 A | 12/1997 | Tajima |
| 5,705,062 A | 1/1998 | Knobel |
| 5,714,380 A | 2/1998 | Neri et al. |
| 5,716,583 A | 2/1998 | Smethers et al. |
| 5,717,148 A | 2/1998 | Ely et al. |
| 5,720,377 A | 2/1998 | Lapeus et al. |
| 5,720,923 A | 2/1998 | Haff et al. |
| 5,721,141 A | 2/1998 | Babson et al. |
| 5,723,092 A | 3/1998 | Babson |
| 5,730,938 A | 3/1998 | Carbonari et al. |
| 5,730,939 A | 3/1998 | Kurumada et al. |
| 5,736,101 A | 4/1998 | Gianino |
| 5,736,105 A | 4/1998 | Astle |
| 5,736,413 A | 4/1998 | Uzan et al. |

(56) References Cited

U.S. PATENT DOCUMENTS

| | | |
|---|---|---|
| 5,738,827 A | 4/1998 | Marquiss |
| 5,741,461 A | 4/1998 | Takahashi et al. |
| 5,741,708 A | 4/1998 | Carey et al. |
| 5,746,977 A | 5/1998 | Imai et al. |
| 5,746,978 A | 5/1998 | Bienhaus et al. |
| 5,748,978 A | 5/1998 | Narayan et al. |
| 5,750,338 A | 5/1998 | Collins et al. |
| 5,762,872 A | 6/1998 | Bühler et al. |
| 5,762,873 A | 6/1998 | Fanning et al. |
| 5,765,490 A | 6/1998 | Colin et al. |
| 5,773,268 A | 6/1998 | Korenberg et al. |
| 5,773,296 A | 6/1998 | Montalbano et al. |
| 5,773,662 A | 6/1998 | Imai et al. |
| 5,779,981 A | 7/1998 | Danssaert et al. |
| 5,786,182 A | 7/1998 | Catanzariti et al. |
| 5,789,252 A | 8/1998 | Fujita et al. |
| 5,795,547 A | 8/1998 | Moser et al. |
| 5,795,784 A | 8/1998 | Arnquist et al. |
| 5,807,523 A | 9/1998 | Watts et al. |
| 5,814,277 A | 9/1998 | Bell et al. |
| 5,816,998 A | 10/1998 | Silverstolpe et al. |
| 5,819,964 A | 10/1998 | Grimard |
| 5,826,129 A | 10/1998 | Hasebe et al. |
| 5,827,478 A | 10/1998 | Carey et al. |
| 5,827,479 A | 10/1998 | Yamazaki et al. |
| 5,827,653 A | 10/1998 | Sammes et al. |
| 5,837,195 A | 11/1998 | Malek et al. |
| 5,843,376 A | 12/1998 | Ishihara et al. |
| 5,846,491 A | 12/1998 | Choperena et al. |
| 5,849,247 A | 12/1998 | Uzan et al. |
| 5,855,847 A | 1/1999 | Oonuma et al. |
| 5,856,194 A | 1/1999 | Arnquist et al. |
| 5,863,506 A | 1/1999 | Farren |
| 5,876,668 A | 3/1999 | Kawashima et al. |
| 5,876,670 A | 3/1999 | Mitsumaki et al. |
| 5,882,594 A | 3/1999 | Kawaguchi et al. |
| 5,882,596 A | 3/1999 | Breeser et al. |
| 5,882,918 A | 3/1999 | Goffe |
| 5,885,353 A | 3/1999 | Strodtbeck et al. |
| 5,885,529 A | 3/1999 | Babson et al. |
| 5,885,530 A | 3/1999 | Babson et al. |
| 5,888,454 A | 3/1999 | Leistner et al. |
| 5,897,783 A | 4/1999 | Howe et al. |
| 5,902,549 A | 5/1999 | Mimura et al. |
| 5,919,622 A | 7/1999 | Macho et al. |
| 5,927,547 A | 7/1999 | Papen et al. |
| 5,928,952 A | 7/1999 | Hutchins et al. |
| 5,935,522 A | 8/1999 | Swerdlow et al. |
| 5,947,274 A | 9/1999 | Taskis et al. |
| 5,948,691 A | 9/1999 | Ekiriwang et al. |
| 5,955,373 A | 9/1999 | Hutchins et al. |
| 5,958,763 A | 9/1999 | Goffe |
| 5,958,791 A | 9/1999 | Roberts et al. |
| 5,965,086 A | 10/1999 | Rose et al. |
| 5,972,295 A | 10/1999 | Hanawa et al. |
| 5,985,215 A | 11/1999 | Sakazume et al. |
| 5,985,670 A | 11/1999 | Markin |
| 5,985,671 A | 11/1999 | Leistner et al. |
| 5,985,672 A | 11/1999 | Kegelman et al. |
| 5,988,869 A | 11/1999 | Davidson et al. |
| 6,002,474 A | 12/1999 | Thomas et al. |
| 6,019,945 A | 2/2000 | Ohishi |
| 6,021,170 A | 2/2000 | Reimer et al. |
| 6,027,691 A | 2/2000 | Watts et al. |
| 6,033,574 A | 3/2000 | Siddiqi |
| 6,033,880 A | 3/2000 | Haff et al. |
| 6,042,786 A | 3/2000 | Oonuma et al. |
| 6,043,880 A | 3/2000 | Andrews et al. |
| 6,051,101 A | 4/2000 | Ohtani et al. |
| 6,056,923 A | 5/2000 | Diamond et al. |
| 6,060,022 A | 5/2000 | Pang et al. |
| 6,063,340 A | 5/2000 | Lewis et al. |
| 6,068,393 A | 5/2000 | Hutchins et al. |
| 6,068,978 A | 5/2000 | Zaun et al. |
| 6,071,395 A | 6/2000 | Lange |
| 6,071,477 A | 6/2000 | Auclair et al. |
| 6,073,732 A | 6/2000 | Angerfors |
| 6,074,615 A | 6/2000 | Lewis et al. |
| 6,080,364 A | 6/2000 | Mimura et al. |
| 6,086,827 A | 7/2000 | Horner et al. |
| 6,096,272 A | 8/2000 | Clark et al. |
| 6,103,193 A | 8/2000 | Iwahashi et al. |
| 6,106,781 A | 8/2000 | Rosenberg |
| 6,110,676 A | 8/2000 | Coull et al. |
| 6,110,678 A | 8/2000 | Weisburg et al. |
| 6,117,392 A | 9/2000 | Hanawa et al. |
| 6,117,398 A | 9/2000 | Bienhaus et al. |
| 6,117,683 A | 9/2000 | Kodama et al. |
| 6,123,819 A | 9/2000 | Peeters |
| 6,143,578 A | 11/2000 | Bendele et al. |
| 6,146,592 A | 11/2000 | Kawashima et al. |
| 6,149,872 A | 11/2000 | Mack et al. |
| 6,156,565 A | 12/2000 | Maes et al. |
| 6,165,778 A | 12/2000 | Kedar |
| 6,174,670 B1 | 1/2001 | Wittwer et al. |
| 6,232,079 B1 | 5/2001 | Wittwer et al. |
| 6,245,514 B1 | 6/2001 | Wittwer |
| 6,261,521 B1 | 7/2001 | Mimura et al. |
| 6,267,927 B1 | 7/2001 | Pomar Longedo et al. |
| 6,277,332 B1 | 8/2001 | Sucholeiki |
| 6,293,750 B1 | 9/2001 | Cohen et al. |
| 6,299,567 B1 | 10/2001 | Forrest et al. |
| 6,300,068 B1 | 10/2001 | Burg et al. |
| 6,300,138 B1 | 10/2001 | Gleason et al. |
| 6,319,718 B1 | 11/2001 | Matsubara et al. |
| 6,332,636 B1 | 12/2001 | Cohen et al. |
| 6,335,166 B1 | 1/2002 | Ammann et al. |
| 6,337,050 B1 | 1/2002 | Takahashi et al. |
| 6,352,861 B1 | 3/2002 | Copeland et al. |
| 6,358,752 B1 | 3/2002 | Durst et al. |
| 6,374,982 B1 | 4/2002 | Cohen et al. |
| 6,375,898 B1 | 4/2002 | Ulrich |
| 6,377,342 B1 | 4/2002 | Coeurveille |
| 6,386,749 B1 | 5/2002 | Watts et al. |
| 6,394,992 B1 | 5/2002 | Sjoeholm |
| 6,399,952 B1 | 6/2002 | Maher et al. |
| 6,436,349 B1 | 8/2002 | Carey et al. |
| 6,444,171 B1 | 9/2002 | Sakazume et al. |
| 6,455,325 B1 | 9/2002 | Tajima |
| 6,461,570 B2 | 10/2002 | Ishihara et al. |
| 6,472,217 B1 | 10/2002 | Richards et al. |
| 6,473,190 B1 | 10/2002 | Dosmann |
| 6,498,037 B1 | 12/2002 | Carey et al. |
| 6,503,751 B2 | 1/2003 | Hugh |
| 6,509,193 B1 | 1/2003 | Tajima |
| 6,517,782 B1 | 2/2003 | Horner et al. |
| 6,517,783 B2 | 2/2003 | Horner et al. |
| 6,521,183 B1 | 2/2003 | Burri et al. |
| 6,522,976 B2 | 2/2003 | Shiba et al. |
| 6,551,833 B1 | 4/2003 | Lehtinen et al. |
| 6,562,298 B1 | 5/2003 | Arnquist et al. |
| 6,569,627 B2 | 5/2003 | Wittwer et al. |
| 6,579,717 B1 | 6/2003 | Matsubara et al. |
| 6,586,234 B1 | 7/2003 | Burg et al. |
| 6,592,818 B2 | 7/2003 | Ishihara et al. |
| 6,597,450 B1 | 7/2003 | Andrews et al. |
| 6,599,749 B1 | 7/2003 | Kodama et al. |
| 6,605,213 B1 | 8/2003 | Ammann et al. |
| 6,632,654 B1 | 10/2003 | Gebrian et al. |
| 6,709,634 B1 | 3/2004 | Okada et al. |
| 6,723,288 B2 | 4/2004 | Devlin, Sr. et al. |
| 6,733,728 B1 | 5/2004 | Mimura et al. |
| 6,752,967 B2 | 6/2004 | Farina et al. |
| 6,764,649 B2 | 7/2004 | Ammann |
| 6,764,650 B2 | 7/2004 | Takahashi et al. |
| 6,776,961 B2 | 8/2004 | Lindsey et al. |
| 6,780,617 B2 | 8/2004 | Chen |
| 6,787,338 B2 | 9/2004 | Wittwer et al. |
| 6,825,921 B1 | 11/2004 | Modlin et al. |
| 6,827,901 B2 | 12/2004 | Copeland et al. |
| 6,846,457 B1 | 1/2005 | Towika et al. |
| 6,866,821 B2 | 3/2005 | Friedlander et al. |
| 6,878,343 B2 | 4/2005 | Sklar et al. |
| 6,890,742 B2 | 5/2005 | Ammann et al. |

(56) References Cited

U.S. PATENT DOCUMENTS

| | | |
|---|---|---|
| 6,911,327 B2 | 6/2005 | McMillan et al. |
| 6,919,058 B2 | 7/2005 | Andersson et al. |
| 6,919,175 B1 | 7/2005 | Bienhaus et al. |
| 6,924,152 B2 | 8/2005 | Matsubara et al. |
| 6,943,029 B2 | 9/2005 | Copeland et al. |
| 6,958,130 B1 | 10/2005 | Gicquel et al. |
| 7,011,792 B2 | 3/2006 | Mimura et al. |
| 7,028,831 B2 | 4/2006 | Veiner |
| 7,029,922 B2 | 4/2006 | Miller |
| 7,033,820 B2 | 4/2006 | Ammann et al. |
| 7,081,226 B1 | 7/2006 | Wittwer et al. |
| 7,105,351 B2 | 9/2006 | Matsubara et al. |
| 7,115,090 B2 | 10/2006 | Lagarde |
| 7,115,384 B2 | 10/2006 | Clark et al. |
| 7,118,892 B2 | 10/2006 | Ammann et al. |
| 7,118,918 B2 | 10/2006 | Copeland et al. |
| 7,118,982 B2 | 10/2006 | Govyadinov et al. |
| 7,132,082 B2 | 11/2006 | Aviles et al. |
| 7,135,145 B2 | 11/2006 | Ammann et al. |
| 7,138,091 B2 | 11/2006 | Lee et al. |
| 7,141,213 B1 | 11/2006 | Pang et al. |
| 7,160,998 B2 | 1/2007 | Wittwer et al. |
| 7,169,356 B2 | 1/2007 | Gebrian et al. |
| 7,171,863 B2 | 2/2007 | Tamura et al. |
| 7,182,912 B2 | 2/2007 | Carey et al. |
| 7,217,513 B2 | 5/2007 | Parameswaran et al. |
| 7,220,589 B2 | 5/2007 | Richards et al. |
| 7,250,303 B2 | 7/2007 | Jakubowicz et al. |
| 7,264,111 B2 | 9/2007 | Veiner |
| 7,267,795 B2 | 9/2007 | Ammann et al. |
| 7,270,783 B2 | 9/2007 | Takase et al. |
| 7,273,749 B1 | 9/2007 | Wittwer et al. |
| 7,276,208 B2 | 10/2007 | Sevigny et al. |
| 7,303,139 B1 | 12/2007 | Rudloff |
| 7,331,474 B2 | 2/2008 | Veiner et al. |
| 7,341,691 B2 | 3/2008 | Tamura et al. |
| 7,360,984 B1 | 4/2008 | Sugiyama et al. |
| 7,361,305 B2 | 4/2008 | Mimura et al. |
| 7,381,370 B2 | 6/2008 | Chow et al. |
| 7,384,600 B2 | 6/2008 | Burns et al. |
| 7,390,458 B2 | 6/2008 | Burow et al. |
| 7,396,509 B2 | 7/2008 | Burns |
| 7,402,281 B2 | 7/2008 | Huynh-Ba et al. |
| 7,407,427 B1 | 8/2008 | Liu |
| 7,407,627 B1 | 8/2008 | Rosenberg et al. |
| 7,482,143 B2 | 1/2009 | Ammann et al. |
| 7,524,652 B2 | 4/2009 | Ammann et al. |
| 7,560,255 B2 | 7/2009 | Ammann et al. |
| 7,560,256 B2 | 7/2009 | Ammann et al. |
| 7,575,937 B2 | 8/2009 | Wiggli et al. |
| 7,611,675 B2 | 11/2009 | Sevigny et al. |
| 7,622,078 B2 | 11/2009 | Pagés Pinyol |
| 7,638,337 B2 | 12/2009 | Ammann et al. |
| 7,641,855 B2 | 1/2010 | Farina et al. |
| 7,666,602 B2 | 2/2010 | Ammann et al. |
| 7,666,681 B2 | 2/2010 | Ammann et al. |
| 7,670,553 B2 | 3/2010 | Babson |
| 7,670,554 B2 | 3/2010 | Chow et al. |
| 7,670,832 B2 | 3/2010 | Wittwer et al. |
| 7,700,042 B2 | 4/2010 | Matsumoto et al. |
| 7,700,043 B2 | 4/2010 | Mimura et al. |
| 7,731,414 B2 | 6/2010 | Vincent et al. |
| 7,731,898 B2 | 6/2010 | Burkhardt et al. |
| 7,745,205 B2 | 6/2010 | Wittwer et al. |
| 7,749,441 B2 | 7/2010 | Hanawa et al. |
| 7,785,534 B2 | 8/2010 | Watari |
| 7,815,858 B2 | 10/2010 | Sevigny et al. |
| 7,827,874 B2 | 11/2010 | Tsujimura et al. |
| 7,837,452 B2 | 11/2010 | Ignatiev et al. |
| 7,842,237 B1 | 11/2010 | Shibuya et al. |
| 7,842,504 B2 | 11/2010 | Devlin, Sr. |
| 7,850,914 B2 | 12/2010 | Veiner et al. |
| 7,854,892 B2 | 12/2010 | Veiner et al. |
| 7,855,084 B2 | 12/2010 | Jakubowicz et al. |
| 7,858,032 B2 | 12/2010 | Le Comte et al. |
| 7,867,777 B2 | 1/2011 | Aviles et al. |
| 7,910,294 B2 | 3/2011 | Karlsen |
| 7,939,036 B2 | 5/2011 | Burkhardt et al. |
| 7,941,904 B2 | 5/2011 | Smith |
| 7,943,100 B2 | 5/2011 | Rousseau |
| 7,947,225 B2 | 5/2011 | Itoh |
| 7,951,329 B2 | 5/2011 | Malyarov et al. |
| 7,964,140 B2 | 6/2011 | Watari |
| 7,985,375 B2 | 7/2011 | Edens et al. |
| 7,998,409 B2 | 8/2011 | Veiner et al. |
| 7,998,432 B2 | 8/2011 | Rousseau |
| 7,998,751 B2 | 8/2011 | Evers et al. |
| 8,003,050 B2 | 8/2011 | Burkhardt et al. |
| 8,012,419 B2 | 9/2011 | Ammann et al. |
| 8,038,941 B2 | 10/2011 | Devlin, Sr. |
| 8,038,942 B2 | 10/2011 | Pang et al. |
| 8,047,086 B2 | 11/2011 | Smith |
| 8,066,943 B2 | 11/2011 | Kegelman et al. |
| 8,071,053 B2 | 12/2011 | Matsuzaki et al. |
| 8,097,211 B2 | 1/2012 | Hamada et al. |
| 8,114,351 B2 | 2/2012 | Degenhardt |
| 8,119,080 B2 | 2/2012 | Wiggli et al. |
| 8,137,620 B2 | 3/2012 | Ammann et al. |
| 8,142,740 B2 | 3/2012 | Self et al. |
| 8,147,777 B2 | 4/2012 | Schacher et al. |
| 8,153,061 B2 | 4/2012 | Walters et al. |
| 8,154,899 B2 | 4/2012 | Degroot |
| 8,158,058 B2 | 4/2012 | Shiba et al. |
| 8,161,831 B2 | 4/2012 | Fukuma |
| 8,163,239 B2 | 4/2012 | Fujita |
| 8,178,043 B2 | 5/2012 | Burkhardt et al. |
| 8,187,558 B2 | 5/2012 | Jacobs et al. |
| 8,192,992 B2 | 6/2012 | Ammann et al. |
| 8,221,682 B2 | 7/2012 | Ammann et al. |
| 8,226,387 B2 | 7/2012 | Ignatiev |
| 8,234,941 B2 | 8/2012 | Fukuda et al. |
| 8,257,650 B2 | 9/2012 | Chow et al. |
| 8,257,664 B2 | 9/2012 | Ogusu |
| 8,262,994 B2 | 9/2012 | Hamada et al. |
| 8,262,999 B2 | 9/2012 | Kaneblei et al. |
| 8,266,973 B2 | 9/2012 | Maeda et al. |
| 8,293,191 B2 | 10/2012 | Kohara et al. |
| 8,309,358 B2 | 11/2012 | Ammann et al. |
| 8,318,500 B2 | 11/2012 | Ammann et al. |
| 8,329,101 B2 | 12/2012 | Fujita |
| 8,333,936 B2 | 12/2012 | Miyashita et al. |
| 8,337,753 B2 | 12/2012 | Ammann et al. |
| 8,343,423 B2 | 1/2013 | Mori et al. |
| 8,343,754 B2 | 1/2013 | Wittwer et al. |
| 8,343,770 B2 | 1/2013 | Hamada et al. |
| 8,354,078 B2 | 1/2013 | Shohmi et al. |
| 8,355,132 B2 | 1/2013 | Xia et al. |
| 8,356,525 B2 | 1/2013 | Hamada et al. |
| 8,357,538 B2 | 1/2013 | Self et al. |
| 8,366,997 B2 | 2/2013 | Degroot |
| 8,383,039 B2 | 2/2013 | Zhou et al. |
| 8,431,079 B2 | 4/2013 | Rosenberg et al. |
| 8,501,496 B2 | 8/2013 | Zuk et al. |
| 8,545,757 B2 | 10/2013 | Utsugi et al. |
| 8,556,564 B2 | 10/2013 | Miller |
| 9,274,133 B2 | 3/2016 | Kraemer et al. |
| 9,335,338 B2 | 5/2016 | Ochranek et al. |
| 10,267,818 B2 | 4/2019 | Ochranek et al. |
| 11,125,766 B2 | 9/2021 | Ochranek |
| 2002/0127147 A1 | 9/2002 | Kacian et al. |
| 2002/0132353 A1 | 9/2002 | Tamura et al. |
| 2002/0134923 A1 | 9/2002 | Watari et al. |
| 2002/0155590 A1 | 10/2002 | Gebrian et al. |
| 2002/0164807 A1 | 11/2002 | Itaya et al. |
| 2002/0169518 A1 | 11/2002 | Luoma, II |
| 2003/0138967 A1 | 7/2003 | Hall et al. |
| 2003/0180815 A1 | 9/2003 | Rawson et al. |
| 2003/0202905 A1 | 10/2003 | Devlin et al. |
| 2004/0114248 A1 | 6/2004 | Hokazono et al. |
| 2004/0115095 A1 | 6/2004 | Devlin, Sr. et al. |
| 2004/0131506 A1 | 7/2004 | Zurcher |
| 2004/0134750 A1 | 7/2004 | Luoma, II |
| 2004/0144474 A1 | 7/2004 | Drummond et al. |
| 2004/0166043 A1 | 8/2004 | Vandine et al. |

(56) References Cited

U.S. PATENT DOCUMENTS

| | | |
|---|---|---|
| 2005/0014285 A1 | 1/2005 | Miller |
| 2005/0106756 A1 | 5/2005 | Blankenstein et al. |
| 2005/0112589 A1 | 5/2005 | Hahn et al. |
| 2005/0142040 A1 | 6/2005 | Hanawa et al. |
| 2005/0153426 A1 | 7/2005 | Muller et al. |
| 2005/0220670 A1 | 10/2005 | Palmieri et al. |
| 2005/0230380 A1 | 10/2005 | Yoshino et al. |
| 2005/0249634 A1 | 11/2005 | Devlin, Sr. |
| 2006/0159587 A1 | 7/2006 | Fechtner et al. |
| 2006/0190735 A1 | 8/2006 | May et al. |
| 2006/0243591 A1 | 11/2006 | Plotkin et al. |
| 2006/0263248 A1 | 11/2006 | Gomm et al. |
| 2006/0281193 A1 | 12/2006 | Petrilla et al. |
| 2006/0286004 A1 | 12/2006 | Jacobs et al. |
| 2006/0290496 A1 | 12/2006 | Peeters |
| 2007/0010019 A1 | 1/2007 | Luoma, II |
| 2007/0059209 A1 | 3/2007 | Pang et al. |
| 2007/0092390 A1 | 4/2007 | Ignatiev et al. |
| 2007/0156129 A1 | 7/2007 | Kovalcheck |
| 2007/0172902 A1 | 7/2007 | Zhang et al. |
| 2007/0270672 A1 | 11/2007 | Hayter |
| 2008/0106755 A1 | 5/2008 | Morooka |
| 2008/0145939 A1 | 6/2008 | Jakubowicz et al. |
| 2008/0190735 A1 | 8/2008 | Luoma |
| 2008/0213742 A1 | 9/2008 | Asgari et al. |
| 2008/0251490 A1 | 10/2008 | Livingston et al. |
| 2008/0269950 A1 | 10/2008 | Greco et al. |
| 2008/0297769 A1 | 12/2008 | Bamberg et al. |
| 2008/0317632 A1 | 12/2008 | Shimasaki et al. |
| 2009/0017491 A1 | 1/2009 | Lemme et al. |
| 2009/0035867 A1 | 2/2009 | Yagi et al. |
| 2009/0081081 A1 | 3/2009 | Kowari et al. |
| 2009/0148345 A1 | 6/2009 | Hamazumi et al. |
| 2009/0215159 A1 | 8/2009 | Kirby |
| 2009/0218704 A1 | 9/2009 | Murakami |
| 2009/0220379 A1 | 9/2009 | Wakamiya et al. |
| 2009/0227033 A1 | 9/2009 | Hamada et al. |
| 2009/0258414 A1 | 10/2009 | Wittwer et al. |
| 2009/0325309 A1 | 12/2009 | Favuzzi et al. |
| 2010/0107784 A1 | 5/2010 | Stein |
| 2010/0111765 A1 | 5/2010 | Gomm et al. |
| 2010/0126286 A1 | 5/2010 | Self et al. |
| 2010/0133292 A1 | 6/2010 | Ware et al. |
| 2010/0140149 A1 | 6/2010 | Fulkerson et al. |
| 2010/0150298 A1 | 6/2010 | Gilmore et al. |
| 2010/0187253 A1 | 7/2010 | Vincent et al. |
| 2010/0205139 A1 | 8/2010 | Xia et al. |
| 2010/0213080 A1 | 8/2010 | Celentano et al. |
| 2010/0233035 A1 | 9/2010 | Denawa et al. |
| 2010/0276445 A1 | 11/2010 | Jacobs et al. |
| 2010/0290952 A1 | 11/2010 | Koike et al. |
| 2010/0330609 A1 | 12/2010 | Nagai et al. |
| 2010/0332144 A1 | 12/2010 | Nagai et al. |
| 2011/0044834 A1 | 2/2011 | Ignatiev |
| 2011/0097240 A1 | 4/2011 | Yamashita et al. |
| 2011/0157580 A1 | 6/2011 | Nogami et al. |
| 2011/0162438 A1 | 7/2011 | Tokieda et al. |
| 2011/0188095 A1 | 8/2011 | Shiraishi |
| 2011/0271773 A1 | 11/2011 | Komatsu et al. |
| 2011/0293475 A1 | 12/2011 | Rosenberg et al. |
| 2011/0303221 A1 | 12/2011 | Kohnle |
| 2011/0312082 A1 | 12/2011 | Silverbrook et al. |
| 2012/0039748 A1 | 2/2012 | Mimura et al. |
| 2012/0039771 A1 | 2/2012 | Utsugi et al. |
| 2012/0114526 A1 | 5/2012 | Watanabe et al. |
| 2012/0152935 A1 | 6/2012 | Kitaizumi et al. |
| 2012/0156764 A1 | 6/2012 | Kondo |
| 2012/0159764 A1 | 6/2012 | Reiger |
| 2012/0183438 A1 | 7/2012 | Shiba et al. |
| 2012/0195808 A1 | 8/2012 | Arras et al. |
| 2012/0206713 A1 | 8/2012 | Nogami et al. |
| 2012/0218854 A1 | 8/2012 | Behringer et al. |
| 2012/0248144 A1 | 10/2012 | Barron |
| 2012/0258004 A1 | 10/2012 | Ignatiev et al. |
| 2012/0294763 A1 | 11/2012 | Fukuda et al. |
| 2012/0301359 A1 | 11/2012 | Kraemer et al. |
| 2013/0017535 A1 | 1/2013 | Frey et al. |
| 2013/0064737 A1 | 3/2013 | Mori et al. |
| 2013/0065797 A1 | 3/2013 | Silbert et al. |
| 2013/0078617 A1 | 3/2013 | Ueda et al. |
| 2013/0089464 A1 | 4/2013 | Sakashita et al. |
| 2013/0112014 A1 | 5/2013 | Hamada et al. |
| 2013/0123089 A1 | 5/2013 | Johns et al. |
| 2013/0125648 A1 | 5/2013 | Murashie et al. |
| 2013/0125675 A1 | 5/2013 | Müller et al. |
| 2013/0129166 A1 | 5/2013 | Mueller et al. |
| 2013/0157380 A1 | 6/2013 | Zhou et al. |
| 2013/0167872 A1 | 7/2013 | Weston et al. |
| 2013/0280129 A1 | 10/2013 | Watanabe et al. |
| 2013/0280130 A1 | 10/2013 | Sarwar et al. |
| 2013/0323758 A1 | 12/2013 | Oguri et al. |
| 2014/0011295 A1 | 1/2014 | Ammann et al. |
| 2014/0093975 A1 | 4/2014 | Wang et al. |
| 2014/0147922 A1 | 5/2014 | Knofe et al. |
| 2014/0248619 A1 | 9/2014 | Ammann et al. |
| 2014/0260089 A1 | 9/2014 | Luoma et al. |
| 2014/0263316 A1 | 9/2014 | Accurso |
| 2014/0269158 A1 | 9/2014 | Luoma, II |
| 2014/0271411 A1 | 9/2014 | Luoma, II et al. |
| 2014/0273242 A1 | 9/2014 | Ochranek et al. |
| 2014/0273245 A1 | 9/2014 | Ochranek et al. |
| 2014/0305227 A1 | 10/2014 | Johns |
| 2014/0322080 A1 | 10/2014 | Sarwar et al. |
| 2014/0339100 A1 | 11/2014 | Malecha |
| 2015/0037211 A1 | 2/2015 | Wang et al. |
| 2015/0079695 A1 | 3/2015 | Pollack et al. |
| 2015/0207334 A1 | 7/2015 | Mitcheson et al. |
| 2015/0224503 A1 | 8/2015 | Dulaff |
| 2015/0226761 A1 | 8/2015 | Mizutani et al. |
| 2015/0241457 A1 | 8/2015 | Miller |
| 2015/0244852 A1 | 8/2015 | Erickson et al. |
| 2015/0286803 A1 | 10/2015 | Myers et al. |
| 2016/0109350 A1 | 4/2016 | Esaki et al. |
| 2016/0167042 A1 | 6/2016 | Tyrrell et al. |
| 2016/0184826 A1 | 6/2016 | Nemoto |
| 2016/0245836 A1 | 8/2016 | Ochranek |
| 2016/0318022 A1 | 11/2016 | Accurso |
| 2016/0349237 A1 | 12/2016 | Klinec et al. |
| 2016/0352329 A1 | 12/2016 | Southern et al. |
| 2016/0370293 A1 | 12/2016 | Parsons et al. |
| 2018/0193498 A1 | 7/2018 | Fritchie et al. |
| 2019/0212354 A1 | 7/2019 | Ochranek |
| 2020/0232982 A1 | 7/2020 | Parsons et al. |
| 2020/0386751 A1 | 12/2020 | Takulapalli |
| 2021/0102232 A1 | 4/2021 | Gonzalez-Macia et al. |
| 2021/0113131 A1 | 4/2021 | Lee et al. |
| 2021/0148902 A1 | 5/2021 | Esquivel Bojorquez et al. |
| 2021/0156855 A1 | 5/2021 | Ranzoni et al. |
| 2022/0011335 A1 | 1/2022 | Ochranek |
| 2022/0250060 A1 | 8/2022 | Werthman |
| 2022/0308049 A1 | 9/2022 | Miller et al. |

FOREIGN PATENT DOCUMENTS

| | | |
|---|---|---|
| CN | 102221625 | 10/2011 |
| CN | 102292645 | 12/2011 |
| CN | 102520200 | 6/2012 |
| CN | 102879591 A | 1/2013 |
| CN | 105745546 A | 3/2018 |
| CN | 107831324 A | 3/2018 |
| CN | 107966576 A | 4/2018 |
| CN | 10574556 B | 5/2020 |
| CN | 107966576 B | 8/2021 |
| CN | 107831324 B | 11/2021 |
| CN | 114137240 | 3/2022 |
| DE | 112010001896 | 6/2012 |
| EP | 576291 | 12/1993 |
| EP | 779514 | 6/1997 |
| EP | 831330 | 3/1998 |
| EP | 0853736 A1 | 7/1998 |
| EP | 856736 | 8/1998 |
| EP | 871892 | 10/1998 |
| EP | 1414573 | 5/2004 |
| EP | 2068154 | 6/2009 |

(56) References Cited

FOREIGN PATENT DOCUMENTS

| | | |
|---|---|---|
| EP | 2362228 | 8/2011 |
| EP | 2808683 | 12/2014 |
| EP | 2972404 A | 1/2016 |
| EP | 2972404 B | 11/2021 |
| EP | 3964839 | 3/2022 |
| ES | 2901756 T3 | 3/2022 |
| JP | 357019667 | 2/1982 |
| JP | 359116047 | 7/1984 |
| JP | 361095248 | 5/1986 |
| JP | 63085459 | 4/1988 |
| JP | S63122264 | 8/1988 |
| JP | H03221866 | 9/1991 |
| JP | H0526883 | 2/1993 |
| JP | H05178891 A | 7/1993 |
| JP | H063361 | 1/1994 |
| JP | 406027004 | 2/1994 |
| JP | 407181129 | 7/1995 |
| JP | H09304396 | 11/1997 |
| JP | H1062432 | 3/1998 |
| JP | H10123136 | 5/1998 |
| JP | H10325839 | 12/1998 |
| JP | H1130618 A | 2/1999 |
| JP | H11258248 | 9/1999 |
| JP | 3000755 | 1/2000 |
| JP | 2001004633 | 1/2001 |
| JP | 2001165937 | 6/2001 |
| JP | 2001228158 | 8/2001 |
| JP | 2001305145 | 10/2001 |
| JP | 2003098180 | 4/2003 |
| JP | 2003161736 A | 6/2003 |
| JP | 2004020457 | 1/2004 |
| JP | 2004505249 | 2/2004 |
| JP | 2004522979 | 7/2004 |
| JP | 2004271265 | 9/2004 |
| JP | 3582240 | 10/2004 |
| JP | 2005128037 | 5/2005 |
| JP | 2005529315 | 9/2005 |
| JP | 2005533641 | 11/2005 |
| JP | 2008003010 A | 1/2008 |
| JP | 2008064680 | 3/2008 |
| JP | 2008180638 | 8/2008 |
| JP | 2008203197 A | 9/2008 |
| JP | 2008224439 | 9/2008 |
| JP | 2008309661 | 12/2008 |
| JP | 2009008552 | 1/2009 |
| JP | 2009031204 | 2/2009 |
| JP | 2009036561 | 2/2009 |
| JP | 2009074911 | 4/2009 |
| JP | 2009145202 | 7/2009 |
| JP | 2009229430 | 10/2009 |
| JP | 2010501859 | 1/2010 |
| JP | 2010078335 | 4/2010 |
| JP | 2010133827 | 6/2010 |
| JP | 2010145377 A | 7/2010 |
| JP | 2010151672 | 7/2010 |
| JP | 2010156716 | 7/2010 |
| JP | 2010181197 | 8/2010 |
| JP | 2010217047 | 9/2010 |
| JP | 2010217115 | 9/2010 |
| JP | 2011027636 | 2/2011 |
| JP | 2011030618 | 2/2011 |
| JP | 2011033426 | 2/2011 |
| JP | 2011149832 | 8/2011 |
| JP | 2011179919 | 9/2011 |
| JP | 2011257427 | 12/2011 |
| JP | 2012021926 | 2/2012 |
| JP | 2012132721 | 7/2012 |
| JP | 2012163567 A | 8/2012 |
| JP | 5026883 B2 | 9/2012 |
| JP | 2012173180 | 9/2012 |
| JP | 2012189611 | 10/2012 |
| JP | 2012230127 | 11/2012 |
| JP | 2012233923 | 11/2012 |
| JP | 2012251804 | 12/2012 |
| JP | 2012251909 | 12/2012 |
| JP | 2012255664 | 12/2012 |
| JP | 2013033036 | 2/2013 |
| JP | 5178891 | 4/2013 |
| JP | 2016516998 A | 6/2016 |
| JP | 6169245 B2 | 7/2017 |
| JP | 2017198695 A | 11/2017 |
| JP | 6345850 B2 | 6/2018 |
| JP | 2018151404 A | 9/2018 |
| JP | 6785820 B2 | 11/2020 |
| JP | 2020201270 A | 12/2020 |
| JP | 7108663 B2 | 7/2022 |
| JP | 2022160472 A | 10/2022 |
| WO | 9315408 | 8/1993 |
| WO | 9722006 | 6/1997 |
| WO | 02086514 A2 | 10/2002 |
| WO | 03018195 | 3/2003 |
| WO | 2007004466 | 1/2007 |
| WO | 2010026837 | 3/2010 |
| WO | 2010032628 | 3/2010 |
| WO | 2010095375 | 8/2010 |
| WO | 2010106885 | 9/2010 |
| WO | 2012114675 | 8/2012 |
| WO | 2012137019 | 10/2012 |
| WO | 2012158541 | 11/2012 |
| WO | 2013053023 | 4/2013 |
| WO | 2013064561 | 5/2013 |
| WO | 2013064562 | 5/2013 |
| WO | 2013111484 | 8/2013 |
| WO | 2014144627 A1 | 9/2014 |

OTHER PUBLICATIONS

National Intellectual Property Administration, P.R. China, "First Office Action", issued in connection with Chinese Patent Application No. 201710832967.X dated Mar. 27, 2020, translation included, 20 pages.
Japanese Patent Office, "Decision of Rejection", issued in connection with Japanese Patent Application No. 2018-098432 dated Apr. 7, 2020, translation included, 10 pages.
European Patent Office, "Examination Report," issued in connection with European Patent Application No. 14717953.5, dated Oct. 1, 2020, 4 pages.
Japanese Patent Office, "First Office Action," issued in connection with Japanese Patent Application No. 2018-098432, dated Jul. 2, 2019, 8 pages.
International Searching Authority, "International Preliminary Report on Patentability and Written Opinion", issued in connection with International patent application No. PCT/US2014/029118, dated Sep. 24, 2015, 6 pages.
European Patent Office, "Communication Pursuant to Rules 161 and 162 EPC", issued in connection with European Patent Application 14717953.5 dated Oct. 23, 2015, 2 pages.
International Searching Authority, "International Search Report and Written Opinion" issued in connection with International patent application No. PCT/US2013/078041, dated Sep. 19, 2014, 16 pages.
International Searching Authority, "International Search Report and Written Opinion", issued in connection with corresponding International patent application No. PCT/US2014/029138, dated Jun. 23, 2014, 8 pages.
International Searching Authority, "International Search Report and Written Opinion", issued in connection with corresponding International patent application No. PCT/US2014/029118, dated Jun. 27, 2014, 9 pages.
International Searching Authority, "Invitation to Pay Additional Fees and, Where Applicable, Protest Fee and Communication Relating to the Results of the Partial International Search", issued in connection with corresponding International patent application No. PCT/US2013/078041, dated Apr. 9, 2014, 6 pages.
United States Patent and Trademark Office, "Office Action", issued in connection with U.S. Appl. No. 14/213,048, dated Apr. 23, 2015, 12 pages.
United States Patent and Trademark Office, "Notice of Allowance and Fee(s) Due", issued in connection with U.S. Appl. No. 14/213,048, dated Jan. 12, 2016, 10 pages.

(56) References Cited

OTHER PUBLICATIONS

United States Patent and Trademark Office, "Notice of Allowance and Fee(s) Due", issued in connection with U.S. Appl. No. 14/213,048, dated Apr. 11, 2016, 4 pages.

United States Patent and Trademark Office, "Office Action", issued in connection with U.S. Appl. No. 14/213,018, dated Apr. 29, 2015, 13 pages.

United States Patent and Trademark Office, Final Rejection, issued in connection with U.S. Appl. No. 14/213,018, dated Jan. 7, 2016, 15 pages.

United States Patent and Trademark Office, "Notice of Allowance and Fee(s) Due", issued in connection with U.S. Appl. No. 14/213,018, dated Mar. 16, 2016, 10 pages.

United States Patent and Trademark Office, "Notice of Allowance and Fee(s) Due", issued in connection with U.S. Appl. No. 14/213,018, dated Jun. 15, 2016, 4 pages.

United States Patent and Trademark Office, "Notice of Allowance and Fee(s) Due", issued in connection with U.S. Appl. No. 14/213,018, dated Jun. 23, 2016, 4 pages.

State Intellectual Property Office of China, "First Office Action," issued in connection with Chinese Patent Application No. 201480028131.9, dated Nov. 3, 2016, 12 pages.

United States Patent and Trademark Office, "Restriction Requirement" issued in connection with U.S. Appl. No. 15/099,000, dated Nov. 3, 2017, 5 pages.

United States Patent and Trademark Office, "Non-Final Office Action" issued in connection with U.S. Appl. No. 15/099,000, dated Feb. 5, 2018, 54 pages.

United States Patent and Trademark Office, "Non-Final Office Action" issued in connection with U.S. Appl. No. 15/099,000, dated Jun. 13, 2018, 22 pages.

United States Patent and Trademark Office, "Notice of Non-Compliant Amendment" issued in connection with U.S. Appl. No. 15/099,000, dated Oct. 3, 2018, 3 pages.

United States Patent and Trademark Office, "Notice of Allowance and Fee(s) Due", issued in connection with U.S. Appl. No. 15/099,000, dated Dec. 6, 2018, 28 pages.

State Intellectual Property Office of China, "First Office Action," issued in connection with Chinese Patent Application No. 201480027844.3, dated Jul. 5, 2016, 22 pages.

National Intellectual Property Administration, P.R. China, "Second Office Action", issued in connection with Chinese Patent Application No. 201710832967.X, dated Dec. 3, 2020, 12 pages.

National Intellectual Property Administration, P.R. China, "Second Office Action", issued in connection with Chinese Patent Application No. 201710834908.6, dated Jan. 8, 2021, 18 pages.

National Intellectual Property Administration, P.R. China, "Third Office Action", issued in connection with Chinese Patent Application No. 201710834908.6 dated May 20, 2021, translation included, 8 pages.

National Intellectual Property Administration, P.R. China, "Notification of the First Office Action and Search Report," issued in connection with Chinese Patent Application No. 201480027844.3, dated Jul. 5, 2016, 22 pages.

European Patent Office, "Extended European Search Report," issued in connection with European Appl. No. 21204389.7, dated Feb. 3, 2022, 7 pages.

Japanese Patent Office, "Office Action", issued in connection with Japanese Application No. 2020-134112, dated Nov. 2, 2021, English translation included, 8 pages.

United States Patent and Trademark Office, "Notice of Allowance and Fee(s) Due," issued in connection with U.S. Appl. No. 16/357,972, dated May 18, 2021, 9 pages.

United States Patent and Trademark Office, "Supplemental Notice of Allowability," issued in connection with U.S. Appl. No. 16/357,972, dated Jul. 8, 2021, 5 pages.

United States Patent and Trademark Office, "Non-Final Office Action," issued in connection with U.S. Appl. No. 16/357,972, dated Jan. 21, 2021, 10 pages.

Japanese Patent Office, "Notice of Reasons for Refusal", issued in connection with Japanese Patent Application No. 2022-114264 dated Jul. 11, 2023, translation included, 8 pages.

Japanese Patent Office, "Decision to Grant a Patent" issued in connection with Japanese Application No. 2022-114264, dated Oct. 31, 2023, 5 pages.

European Patent Office, "Communication pursuant to Rule 70(1) EPC - Intention to Grant," issued in connection with European Patent Application No. 21 204 389.7-1020, dated Oct. 2, 2023, 49 pages.

AUTOMATED DIAGNOSTIC ANALYZERS HAVING REAR ACCESSIBLE TRACK SYSTEMS AND RELATED METHODS

RELATED APPLICATIONS

This patent arises from a continuation of U.S. application Ser. No. 16/357,972 (now U.S. Pat. No. 11,125,766), titled "Automated Diagnostic Analyzers Having Rear Accessible Track Systems and Related Methods," filed Mar. 19, 2019, which is a continuation U.S. application Ser. No. 15/099,000 (now U.S. Pat. No. 10,267,818), titled "Automated Diagnostic Analyzers Having Rear Accessible Track Systems and Related Methods," filed Apr. 14, 2016, which is a continuation of U.S. application Ser. No. 14/213,048 (now U.S. Pat. No. 9,335,338), titled "Automated Diagnostic Analyzers Having Rear Accessible Track Systems and Related Methods," filed Mar. 14, 2014, which claims the benefit under 35 U.S.C. § 119(e) to U.S. Provisional Application No. 61/794,311, titled "Automated Diagnostic Analyzers Having Rear Accessible Track Systems and Related Methods," and filed Mar. 15, 2013. U.S. application Ser. No. 16/357,972; U.S. application Ser. No. 15/099,000; U.S. application Ser. No. 14/213,048; and U.S. Provisional Application No. 61/794,311 are incorporated herein by this reference in their entireties.

FIELD OF THE DISCLOSURE

The present disclosure relates generally to automated diagnostic analyzers and, more particularly, to automated diagnostic analyzers having rear accessible track systems and related methods.

BACKGROUND

Healthcare diagnostics laboratories use diagnostic instruments for testing and analyzing specimens or samples. Known automated diagnostic analyzers employ multiple carousels and multiple pipetting mechanisms to automatically aspirate liquid from and dispense liquid to different areas in the analyzer to perform diagnostic analysis procedures. The carousels may include a carousel for reaction vessels and a carousel for reagents. By arranging multiple containers on the respective carousels, these known analyzers are capable of conducting multiple assays on multiple test samples as the carousels rotate. These analyzers typically include a pipetting mechanism that aspirates a sample from a sample container and dispenses the sample into one or more reaction vessels on one of the carousels. A robotic device is utilized to individually transport a single sample container at a time to a region near the sample pipetting mechanism for aspiration.

DETAILED DESCRIPTION

Figure 1A:
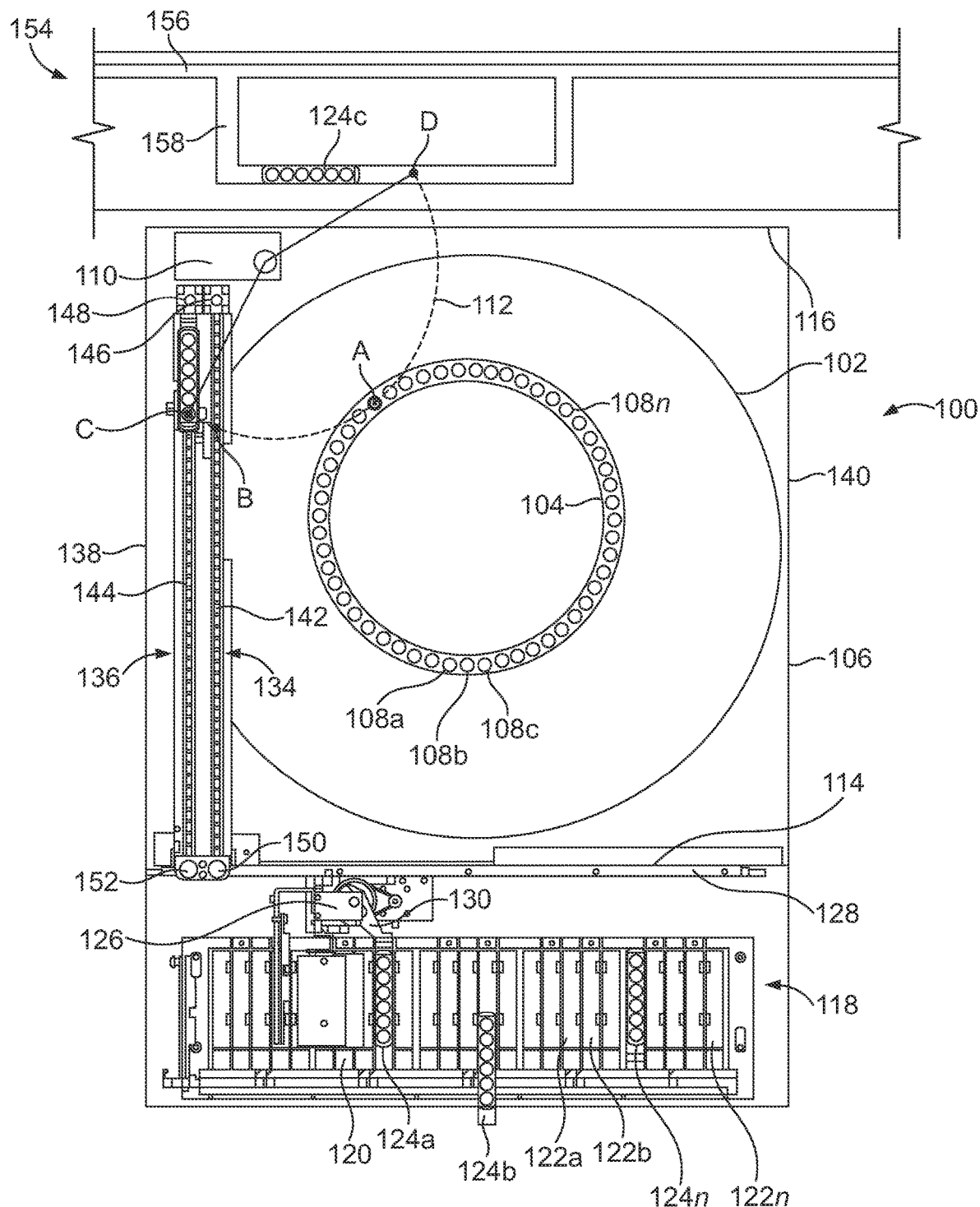
FIG. 1A is a top view of an example analyzer having an example sample positioner in a first position in accordance with the teachings of this disclosure.

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

Diagnostics laboratories employ diagnostic instruments such as those for testing and analyzing specimens or samples including, for example, clinical chemistry analyzers, immunoassay analyzers and hematology analyzers. Specimens and biological samples are analyzed to, for example, check for the presence or absence of an item of interest including, for example, a specific region of DNA, mitochondrial DNA, a specific region of RNA, messenger RNA, transfer RNA, mitochondrial RNA, a fragment, a complement, a peptide, a polypeptide, an enzyme, a prion, a protein, an antibody, an antigen, an allergen, a part of a biological entity such as a cell or a viron, a surface protein, and/or functional equivalent(s) of the above. Specimens such as a patient's body fluids (e.g., serum, whole blood, urine, swabs, plasma, cerebra-spinal fluid, lymph fluids, tissue solids) can be analyzed using a number of different tests to provide information about the patient's health.

Generally, analysis of a test sample involves the reaction of test samples with one or more reagents with respect to one or more analytes. The reaction mixtures are analyzed by an apparatus for one or more characteristics such as, for example, the presence and/or concentration of a certain analyte in the test sample. Use of automated diagnostic analyzers improves the efficiency of the laboratory procedures as the technician (e.g., an operator) has fewer tasks to perform and, thus, the potential for operator or technician error is reduced. In addition, automated diagnostic analyzers also provide results much more rapidly and with increased accuracy and repeatability.

Automated diagnostic analyzers use multiple pipettes to move liquids between storage containers (e.g., receptacles such as open topped tubes) and containers in which the specimens are to be processed (e.g., reaction vessels). For example, a specimen may be contained in a tube that is loaded in a rack on an analyzer, and a head carrying a pipette moves the pipette into the tube where a vacuum is applied to extract a selected amount of the specimen from the tube into the pipette. The head retracts the pipette from the tube and moves the pipette to another tube or reaction vessel located at a processing station, depositing the extracted amount of the specimen from the pipette into the reaction vessel. A reagent is similarly acquired from a reagent supply.

In other examples, a track or positioner (e.g., a robotic device) is disposed at the front of an analyzer to move a sample tube or a sample carrier to a position near a pipette such that the pipette can aspirate from the sample tube. In such examples, a loading bay or rack is disposed on the front side of the analyzer to receive and hold multiple carriers, which may contain, for example, samples and/or reagents to be used in the diagnostic testing. To position samples for testing, the positioner retrieves the carrier from the loading bay and transfers the carrier to a location near an operating range of the sample pipette, which is also adjacent the front of the analyzer. After aspiration, the positioner transports the sample carrier back to the loading bay and reloads the sample carrier in a respective slot. The positioner may then retrieve a second carrier and likewise transfers the second carrier to the location near the sample pipette.

However, the pipetting mechanisms of these known analyzers are only able to aspirate samples from sample tubes that are positioned in a specific location by the positioner. In addition, because only one positioner is utilized, the positioner can only retrieve and hold one carrier at a time and, thus, there are increased time delays between aspirations from different carriers.

Additionally, for some diagnostic testing, some samples may have a higher priority for testing, some samples and/or reagents may need to be refrigerated and/or other samples and/or reagents may involve additional processing steps (e.g., centrifugation, incubation) prior to analysis. Some known laboratories use a laboratory automated system having a track to transport priority samples and other liquids (e.g., reagents, calibration fluids, control fluids, wash fluids, etc.) to the analyzers. In some known configurations, the track is located along a side of the analyzer and transports the priority samples to a location within the operating range of the sample pipetting mechanism. This arrangement increases the footprint of the analyzer particularly in configurations in which multiple analyzers (e.g., modules) are arranged next to each other. Also, the track system being disposed on the sides of the analyzers prevents the alignment (e.g., a side-by-side layout) of multiple modules, and in some examples, it may be desired to add multiple modules (e.g., analyzers) to increase throughput of a laboratory or facility utilizing the analyzers. In other known configurations, the track system is disposed along the front of the analyzers outside of the front loading bay. However, with this arrangement, additional robotic mechanisms and/or spurs are needed to move the carriers from the track system to the loading bay, and then from the loading bay into the analyzer. Additionally, with this arrangement, the track system blocks access to the front loading bay and, thus, an operator or technician is not able to manually load samples and/or reagents for diagnostic testing.

The example analyzers disclosed herein have a sample pipette (e.g., a pipetting mechanism) disposed near a rear side of the analyzer and one or more shuttle carriers to transport sample carriers from a front side of the analyzer to the rear side of the analyzer near the sample pipette. The sample pipette is positioned to aspirate sample liquid from sample tubes in the carriers and to dispense the sample liquid into one or more reaction vessels in the analyzer.

In some examples, the analyzer includes two carrier shuttles that operate independently of each other, which decreases time between aspirations and, thus, increases throughput of the analyzer. Additionally, by locating the sample pipette adjacent the rear side of the analyzer, a laboratory automated system (LAS) track can be disposed (e.g., mounted) at or along the rear side of analyzer without interfering with the layout of the laboratory. For example, multiple modules or analyzers may be aligned side-by-side, and the LAS track may traverse along the rear side of the modules for delivering additional samples (e.g., priority samples) and sample carriers to the individual analyzers. Therefore, the example analyzers may perform diagnostic testing according to traditional protocols or schedules that utilize the front loading bay and may also receive priority samples and other liquids (e.g., calibration/control liquids) from the LAS without interrupting normal operations of the analyzer. Additionally, the modularity of the example analyzers allows more or less analyzers (e.g., one, two, three, four or more) to be utilized depending on the demand (e.g., increased demand for immunoassay testing and/or clinical chemistry testing) of the laboratory or facility. In examples with multiple analyzers, the analyzers may be any combination of immunoassay or clinical chemistry analyzers. For example, there may be a laboratory system with three immunoassay analyzers coupled as modules with a clinical chemistry analyzer. In other examples, there may be two of each and/or other combinations are possible.

An example apparatus disclosed herein includes an analyzer to perform a diagnostic test, the analyzer having a first side and a second side opposite the first side. The example apparatus includes a loading bay disposed on the first side of the analyzer to receive a first carrier and a pipetting mechanism coupled to the analyzer adjacent the second side. The example apparatus also includes a first carrier shuttle to transport the first carrier from a first location adjacent the loading bay to a second location adjacent the pipetting mechanism. In addition, the example apparatus includes a track disposed adjacent the second side of the analyzer to transfer a second carrier to a third location adjacent the pipetting mechanism.

In some examples, the apparatus also includes a second carrier shuttle, wherein the loading bay is to receive a third carrier and the second carrier shuttle is to transport the third carrier from the first location adjacent the loading bay to the second location adjacent the pipetting mechanism. In some such examples, the first carrier shuttle and the second carrier shuttle are independently movable. In some examples, the apparatus also includes a positioner to transport the first carrier from a slot in the loading bay to the first carrier shuttle. In some such examples, the positioner is to transport the third carrier from a slot in the loading bay to the second carrier shuttle.

In some examples, the first carrier shuttle comprises a lead screw. In some examples, the first carrier shuttle comprises a conveyor belt.

In some examples, the first carrier shuttle is to move in a direction substantially perpendicular to the track. In some examples, the track comprises a spur to transport the first carrier to or from the third location.

In some examples, the apparatus also includes a motor to operate the first carrier shuttle, the motor being disposed at one of the first location or the second location. In some such examples, the apparatus also includes a sensor to detect movement in the first carrier shuttle, the sensor disposed at the other of the first location or the second location, opposite the motor.

In some examples, the analyzer comprises a rotatable plate having a plurality of reaction vessels, and the pipetting mechanism is to dispense liquid into one or more of the reaction vessels. In some such examples, the pipetting mechanism is to follow a first protocol of liquid transfer between at least one of the second location or the third location and the reaction vessels. In some examples, the first protocol to be suspended, the first carrier shuttle or a second carrier shuttle is to transport a third carrier from the loading bay to the second location, and the pipetting mechanism is to transfer liquid between the third carrier and at least one of the reaction vessels.

In some examples, the track is coupled to a refrigerated storage area. In some examples, the pipetting mechanism is to at least one of dispense or aspirate a sample from the second location and the third location.

Another example apparatus disclosed herein includes a first carousel, a second carousel, a first track on a first side of the first carousel, a second track on a second side of the first carousel parallel to the first track, a third track on a third side of the first carousel and a pipette to access the first carousel, the first track and the third track.

In some examples, the pipette is to pivot about a single axis to access each of the first carousel, the first track and the third track. In some examples, the third track is perpendicular to the first track. In some examples, the third track comprises a first shuttle to transport a carrier from a first position near the second track to a second position near the pipette. In some examples, the third track comprises a first shuttle and a second shuttle. In some examples, the first shuttle and second shuttle are independently movable. In some examples, the first carousel is to carry a reaction vessel and the second carousel is to carry a reagent container.

An example method is disclosed here that includes transporting a first carrier from a first side of an analyzer having a loading bay to a second side of the analyzer opposite the first side, aspirating a first liquid from the first carrier using a pipetting mechanism disposed adjacent the second side of the analyzer, and dispensing the first liquid, via the pipetting mechanism, into a first reaction vessel on the analyzer. The example method includes transporting a second carrier along a track to a position adjacent the pipetting mechanism, the track disposed along the second side of the analyzer, aspirating a second liquid from the second carrier using the pipetting mechanism, and dispensing the second liquid, via the pipetting mechanism, into a second reaction vessel on the analyzer.

In some examples, the first carrier is transported to the second side of the analyzer via a first carrier shuttle. In some such examples, the method includes transporting a third carrier from the first side of the analyzer to the second side of the analyzer. In some examples, the method includes aspirating a third liquid from the third carrier using the pipetting mechanism and dispensing the third liquid, via the pipetting mechanism, into a third reaction vessel on the analyzer. In some examples, the third carrier is transported to the second side of the analyzer via a second carrier shuttle. In some examples, the first carrier shuttle and the second carrier shuttle operate independently of each other. In some examples, one or more of the first carrier shuttle or the second carrier shuttle is a track comprising a lead screw. In some examples, one or more of the first carrier shuttle or the second carrier shuttle is a track comprising a conveyor belt. In some examples, one or more of the first carrier, the second carrier or the third carrier comprises at least one test sample tube.

Also disclosed herein is an example system that includes multiple analyzers. For example, the example system includes a first analyzer to perform a first diagnostic test and a second analyzer to perform a second diagnostic test. The example first analyzer includes a first proximal side, a first distal side opposite the first proximal side, a first pipetting mechanism adjacent the first distal side and a first loading bay disposed on the first proximal side to receive a first carrier. The example analyzer also includes a first carrier shuttle to transport the first carrier from a first location adjacent the first proximal side to a second location adjacent the first pipetting mechanism. The example second analyzer includes a second proximal side, a second distal side opposite the second proximal side, a second pipetting mechanism adjacent the second distal side and a second loading bay disposed on the second proximal side to receive a second carrier. In addition, the example second analyzer includes a second carrier shuttle to transport the second carrier from a third location adjacent the second proximal side of the second analyzer to a fourth location adjacent the second pipetting mechanism. Also, the example system includes a track disposed along the first distal side and the second distal side. The example track includes a first sidetrack to transfer a third carrier to a fifth location adjacent the first pipetting mechanism.

In some example, the example track includes a second sidetrack to transfer the third carrier to a sixth location adjacent the second pipetting mechanism.

In some examples, the first carrier shuttle and the second carrier shuttle are substantially parallel. In some examples, the first carrier shuttle is substantially perpendicular to the track.

In some examples, the first diagnostic test is an immunoassay and the second diagnostic test is a clinical chemistry assay. Also, in some examples, the first diagnostic test is an immunoassay and the second diagnostic test is an immunoassay. In addition, in some examples, the first diagnostic test is a clinical chemistry assay and the second diagnostic test is a clinical chemistry assay.

In some examples, the example system also includes a positioner disposed along the first proximal side and the second proximal side of the second analyzer. In some examples, the positioner is to transfer the second carrier from the second loading bay to the first carrier shuttle on the first analyzer.

In example system also may include a third analyzer disposed next to one of the first analyzer or the second analyzer. The example third analyzer includes a third proximal side, a third distal side opposite the third proximal side, a third pipetting mechanism adjacent the third distal side and a third loading bay disposed on the third proximal side to receive a fourth carrier. In addition, the example third analyzer includes a third carrier shuttle to transport the fourth carrier from a sixth location adjacent the third proximal side of the third analyzer to a seventh location adjacent the third pipetting mechanism. In some examples, the example track of the example system also is disposed along the third distal side of the third analyzer.

Figure 1B:
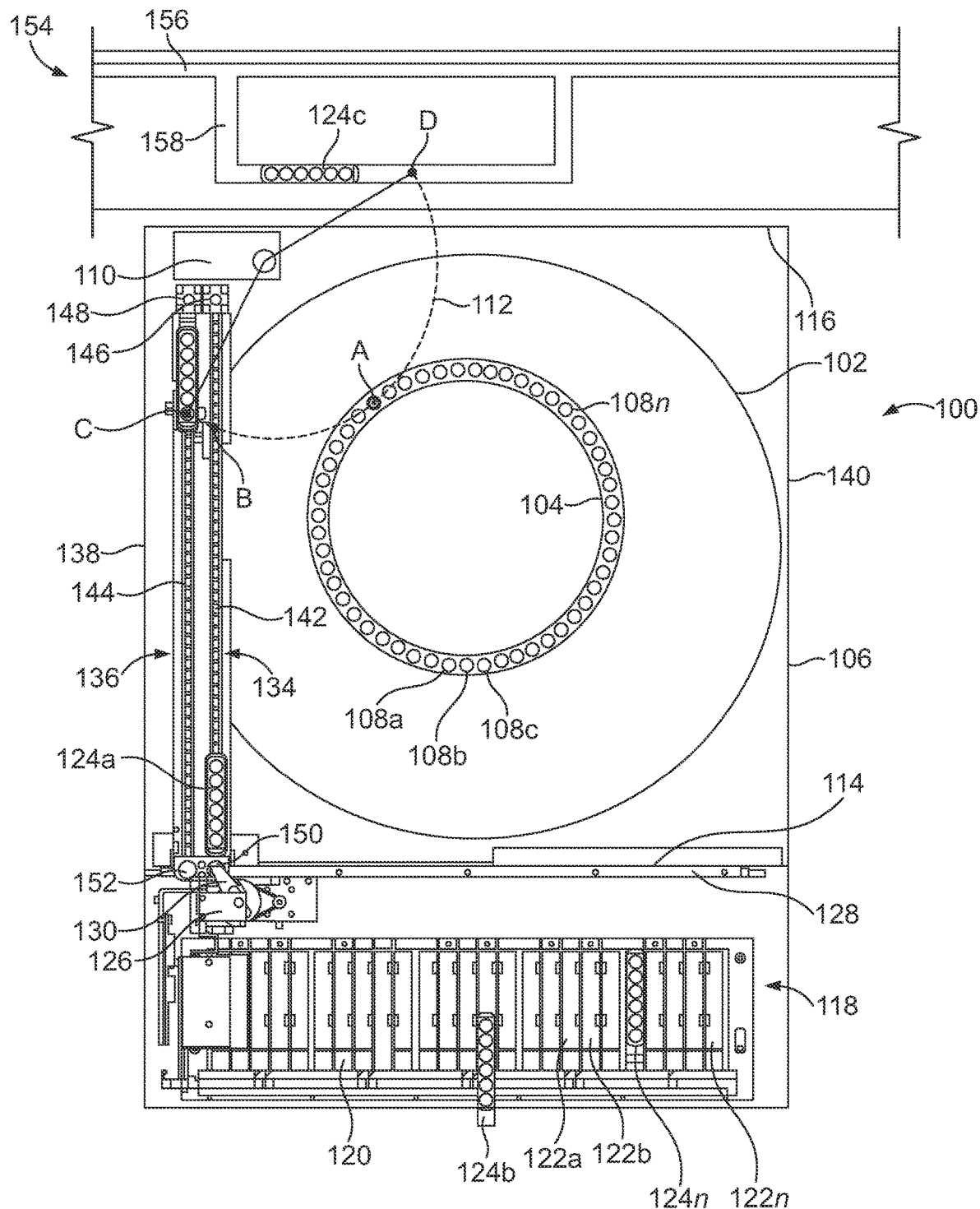
FIG. 1B shows the example analyzer of FIG. 1A with the example positioner in a second position.

Turning now to the figures, an example automated diagnostic analyzer 100 is shown in FIGS. 1A and 1B as having a first carousel 102 and a second carousel 104. The analyzer 100 may be used, for example, to perform immunoassays, clinical chemistry tests, or any other diagnostics tests. The first carousel 102 and the second carousel 104 are rotatably coupled to a base station 106 independent of each other. The base station 106 houses different subassemblies and other components used for testing (e.g., performing diagnostic analyses) such as, for example, wash liquid, bulk reagents, a vacuum source, a pressure source, a refrigeration system, temperature sensors, a processor, motors, etc.

In the example shown, the second carousel 104 is vertically distanced (e.g., spaced) above the first carousel 102 and at least a portion of the second carousel 104 is disposed above and over the first carousel 102. In other examples, the first carousel 102 and the second carousel 104 are disposed next to each other (e.g., coplanar) or may be arranged to be concentric with each other.

In the illustrated example of FIGS. 1A and 1B, the first carousel 102 is a reagent carousel and the second carousel 104 is a reaction vessel carousel. However, in other examples, the first and second carousels 102, 104 may hold reagents, samples, reaction vessels or any combination thereof. In the illustrated examples, the first carousel 102 includes a plurality of reagent containers (including, for example, liquids having microparticles) arranged annularly around the carousel. In some examples, the first carousel 102 has an inner annular array of reagent containers and outer annular array of reagent containers, concentric with the inner annular array of containers. In the example shown, the second carousel 104 is a plate having a plurality of reaction vessels 108a-n disposed around an outer circumference of the plate. In some examples, the reaction vessels 108a-n are reusable cuvettes (e.g., washable glass cuvettes). After a test has been completed in a reaction vessel, the vessel is cleaned (e.g., sterilized) and the vessel may be used for another test. However, in other examples, the reaction vessels 108a-n are disposable cuvettes (e.g., plastic cuvettes) that are discarded after one or more tests. In operation, the second carousel 104 rotates as one or more assay tests are carried out in the reaction vessels 108a-n. A plurality of different modules or instruments may be disposed around the second carousel 104 to, for example, dispense reagents, mix the contents of the reaction vessels, incubate the contents of the reaction vessels, analyze the contents, wash the reaction vessels, etc.

The example automated diagnostic analyzers disclosed herein also include one or more pipetting mechanisms (e.g., probe arms, automated pipettes, pipettes, etc.) to aspirate and dispense liquids within the reaction vessels 108a-n on the second carousel 104. In the illustrated example shown in FIGS. 1A and 1B, the analyzer 100 includes a pipetting mechanism 110 (e.g., a sample pipette) that is coupled (e.g., mounted) to the base station 106. The pipetting mechanism 110 has multiple degrees of freedom. In the example shown, the pipetting mechanism 110 has a path of travel 112 (e.g., an arc path, a horizontal arc path, a radius of travel, an operating range), such that the pipetting mechanism 110 can aspirate (e.g., draw liquid) from or dispense liquid to containers located along the path of travel 112. As shown, the pipetting mechanism 110 is positioned to have access to one of the reaction vessels 108a-n on the second carousel 104 at point A. In some examples, the pipetting mechanism 110 has an axis of rotation and rotates a probe arm with a pipette disposed at the distal end of the probe arm. The pipetting mechanism 110 is also movable in the Z direction (e.g., the vertical direction).

In the example shown, the pipetting mechanism 110 is disposed outside of the first carousel 102 and outside of the second carousel 104, for example, coupled to the base 106 in a position at a distance from the center of the first carousel 102 and the center of the second carousel 104 that is greater than either a first diameter of the first carousel 102 or a second diameter of the second carousel 104. However, in other examples, the pipetting mechanism 110 is disposed above and over the first carousel 102 and/or adjacent the second carousel 104. In such examples, the pipetting mechanism 110 may be mounted to a platform that is disposed between the first carousel 102 and the second carousel 104. In still other examples, the pipetting mechanism 110 may be disposed over the first carousel 102 and over the second carousel 104.

In the example shown in FIGS. 1A and 1B, the example analyzer 100 has a first side 114 (e.g., a front side) and a second side 116 (e.g., a back side, a rear side) opposite the first side 114. The pipetting mechanism 110 is disposed near (e.g., adjacent, along, next to, closer to, bordering) the second side 116 of the analyzer 100. The analyzer 100 also includes a random sample handler (RSH) 118 (e.g., a loading bay) on the first side 114 of the analyzer 100 for accepting and retaining carriers having samples and/or reagents that are to be used for diagnostic testing. In the example shown, the RSH 118 includes a loading rack 120 having a plurality of slots 122a-n for receiving containers, carriers and/or trays of carriers. In the example shown, a plurality of carriers 124a-n have been inserted into the slots 122a-n in the loading rack 120. The carriers 124a-n may hold one or more containers (e.g., a tube, a vessel, an open top container, a vial, a cup, etc.). The containers may include samples, reagents, calibrations, control liquids, etc., used by the analyzer 100 for assay diagnostic testing. In some examples, an operator (e.g., a laboratory technician) loads the carriers 124a-n individually or in trays into the loading rack 120 of the RSH 118. In other examples, an automated track system transports the carriers 124a-n to the RSH 118 and loads the carriers 124a-n into respective ones of the slots 122a-n, for example, via a robotic mechanism.

In FIGS. 1A and 1B, a number of carriers 124a-n have been shown as inserted into different slots 122a-n. In the example shown, each of the carriers 124a-n is holding six containers. However, in other examples, the carriers 124a-n can be configured to hold more or fewer containers depending on the analyzer, the RSH design parameters and/or the carrier layout. The carriers 124a-n are held in the slots 122a-n until selected for testing or retesting.

In the example shown, the RSH 118 includes a positioner 126, which may be a robotic device, to transport the carriers 124a-n and containers coupled thereto to and from the loading rack 120. The positioner 126 is movable along a positioner track 128 disposed along the length of the loading rack 120 and the first side 114 of the analyzer 100. The positioner 126 has an arm 130 to engage the carriers 124a-n loaded in the RSH 118. The positioner 126 and the arm 130 operate to remove the carriers 124a-n from their respective slots 122a-n and transport the carriers 124a-n to different locations along the positioner track 128.

In the example shown in FIGS. 1A and 1B, the example analyzer 100 also includes a first carrier shuttle 134 (e.g., a transporter) and a second carrier shuttle 136 that are disposed near (e.g., along, adjacent, next to, bordering) a third side 138 (e.g., the left side of FIGS. 1A and 1B) of the analyzer 100, opposite a fourth side 140 (e.g., the right side of FIGS. 1A and 1B) of the analyzer 100. In the example shown, the first side 114, the second side 116, the third side 138 and the fourth side 140 define the outer boundaries of the analyzer 100. In the example shown, the analyzer 100 has a rectangular cross-section or footprint. However, in other examples, the analyzer 100 has a square cross-section, a circular cross-section, or any other shaped cross-section or footprint.

In the example shown, the positioner 126 transports the carriers 124a-n to and from the first carrier shuttle 134 and/or the second carrier shuttle 136. For example, in FIG. 1A, the positioner 126 engages the first carrier 124a in the loading rack 120 of RSH 118. The positioner 126 transports the first carrier 124a to, in this example, the first shuttle 134, as shown in FIG. 1B, where the positioner 126 releases or otherwise transfers the first carrier 124a onto the first carrier shuttle 134. The positioner 126 is controlled by a programmable computer for moving the carriers 124a-n as needed and/or desired (e.g., according to scheduling protocols or timetables) for testing. The RSH 118 provides random access to the carriers 124a-n on the loading rack 120. The analyzer 100 includes software that allows users to flexibly configure rules or criteria for testing samples. The software may be programmed into and/or operated from an example processor 316 (FIG. 3), which is disclosed in more detail below.

In some examples, the positioner 126 includes a label reader such as, for example, a barcode reader, a radio frequency identification (RFID) reader and/or other type of reader, to read carrier and container information. The label reader reads the labels attached to the carriers, the sample tubes and/or reagent tubes as the positioner 126 passes the carriers by the reader. An example RSH and an example positioner are disclosed in U.S. patent application Ser. No. 12/106,755, titled "ASSAY TESTING DIAGNOSTIC ANALYZER," filed on Apr. 21, 2008, which is incorporated herein by reference in its entirety.

In the illustrated example, the first and second carrier shuttles 134, 136 operate to move carriers (e.g., the carriers 124a-n) and/or containers between a first position near the first side 114 of the analyzer 100 (e.g., adjacent the rack 120 or the RSH 118) and a second position near the second side 116 of the analyzer 100 (e.g., near the pipetting mechanism 110). Specifically, the first and second carrier shuttles 134, 136 operate to transport carriers 124a-n to a position within the path of travel 112 of the pipetting mechanism 110, such that liquid (e.g., a sample, a specimen) within the containers on the carriers 124a-n can be aspirated from the containers via the pipetting mechanism 110. The pipetting mechanism 110 may then dispense the liquid at point A into one or more of the reaction vessels 108a-n on the second carousel 104 for testing.

In the example shown, the first carrier shuttle 134 includes a first track 142 and the second carrier shuttle 136 includes a second track 144. In some examples, the first track 142 and the second track 144 are conveyor belts that move to transport carriers placed on the respective tracks 142, 144 from one position to another position along the first and second tracks 142, 144. In other examples, the first and second tracks 142, 144 include other track devices such as, for example, a belt, a chain, a carriage, a lead screw, an air cylinder, and/or a linear motor or combinations thereof. In some examples, the first carrier shuttle 134 and the second carrier shuttle 136 comprise different types of tracks. In the example shown, the first carrier shuttle 134 includes a first motor 146 (e.g., an electric motor, a servo motor, a stepper motor, etc.) to drive the first track 142 and the second carrier shuttle 136 includes a second motor 148 to drive the second track 144. In this example, the first and second tracks 142, 144 are operated independently of each other. In other examples, the operations of the first and second tracks 142, 144 are coordinated. The first and second motors 146, 148 may be used to rotate one or more pulleys or gears, which, in turn, move the tracks 142, 144. In the example shown, the first and second motors 146, 148 are rotatable in either direction to move the first and second tracks 142, 144, respectively, in either direction.

In the example shown, the first and second motors 146, 148 are located closer to the second side 116 of the analyzer 100. In the example shown, the first and second carrier shuttles 134, 136 also include respective sensors 150, 152 such as, for example, a linear encoder and/or a transducer. The first and second sensors 150, 152 are located adjacent the first and second tracks 142, 144 to sense a position/movement of the respective tracks 142, 144. Thus, the first and second sensors 150, 152 provide feedback to the first and second motors 146, 148 to indicate whether the first and second tracks 142, 144 are actually moving when the first and second motors 146, 148 are operating. In the example shown, the first and second sensors 150, 152 are positioned on the first and second carrier shuttles 134, 136 opposite the first and second motors 146, 148 as a safety feature to ensure that the tracks 142, 144 are moving when the motors 146, 148 are operating. In some instances, the first and/or second tracks 142, 144 may become dislodged, misaligned or otherwise inoperative and, thus, will not properly transport the carriers. In such an instances, the first and second motors 146, 148 may continue to operate (e.g., spin, rotate, etc.) according to a programmed testing protocol. If the sensors 150, 152 were located adjacent the first and second motors 146, 148, the continued operation of the motors 146, 148 could interfere with the readings of the sensors 146, 148, and cause the sensors 150, 152 to erroneously indicate that the tracks 142, 144 were operating normally. By locating the sensors 150, 152 at the opposite end of the carrier shuttles 134, 136 than the motors 146, 148, the sensors 150, 152 can ensure the tracks 134, 136 are actually moving in accordance with the programming of the first and second motors 146, 148. In some examples, the motors 146, 148 are disposed at, near or closer to the second side 116 of the analyzer 100, and the sensors 150, 152 are at, near or closer to the first side 114 of the analyzer 100. In other examples, this configuration may be switched, such that the motors 146, 148 are disposed at, near or closer to the first side 114 of the analyzer 100, and the sensors 150, 152 are disposed at, near or closer to the second side 116 of the analyzer 100.

The use of multiple shuttle carriers 134, 136 enables the example analyzer 100 to perform sampling (e.g., aspirating and/or dispensing) from one carrier on one track while another carrier is being loaded onto the other track. For example, a first carrier 124a can be retrieved from the RSH 118 by the positioner 126 (FIG. 1A) and deposited on the first track 142 of the first carrier shuttle 134 (FIG. 1B). In some examples, the arm 130 of the positioner 126 includes a hook to engage a tab on the end of the carrier. In other examples, the arm 130 has a gripping mechanism to grip the sides of the carrier. In either example, the arm 130 is used to grab the first carrier 124a from its respective slot 122a-n in the loading rack 120 (FIG. 1A) and then lifts to extract the first carrier 124a from of its respective slot 122a-n. After the positioner 126 retrieves the first carrier 124a, the positioner 126 moves (e.g., slides, translates) along the positioner track 128 towards the third side 138 of the analyzer 100 and, thus, towards the first and second carrier shuttles 134, 136. The arm 130 of the positioner 126 then rotates to align the first carrier on the first track 142 of the first carrier shuttle 134, as shown in the position in FIG. 1B. In the example shown, the arm 130 is capable of rotating at least about 180°.

After the first carrier 124a is placed on the first track 142 of the first carrier shuttle 134, the first motor 146 operates to move the first carrier 124a, via the first track 142, from a first position near the first side 114 of the analyzer 100 to a second position near the second side 116 of the analyzer 100 and, thus, within the path of travel 112 of the pipetting mechanism 110. The pipetting mechanism 110 may aspirate from a container on the first track 142 along the first path of travel 112 at point B. The first motor 146 operates to position the first carrier 124a so that the first path of travel 112 intersects the appropriate container on the first carrier. After aspirating from a container, the pipetting mechanism 110 moves along its first path of travel 112 to dispense the liquid into one or more of the reaction vessels 108a-n on the second carousel 104 at point A.

While the pipetting mechanism 110 is aspirating from a container on the first carrier 124a, the positioner 126 can retrieve a second carrier 124b-n from the RSH 118 and load the second carrier 124b-n onto the second track 144 of the second carrier shuttle 136. The second motor 148 operates to move the second carrier 124b-n on the second track 144 from the first position near the first side 114 of the analyzer 100 to the second side 116 of the analyzer 100 near the pipetting mechanism 110. The second motor 148 operates to position the second carrier 124*b-n* along the first path of travel 112 of the pipetting mechanism 110 (e.g., the position shown in FIGS. 1A and 1B). The pipetting mechanism 100 may aspirate from a container on the carrier 124*b-n* on the second track 144 at point C. As the second carrier shuttle 136 transports the second carrier 124*b-n* to/from the second position near the second side 116, and/or as the pipetting mechanism 110 aspirates from the second carrier 124*b-n*, the first carrier shuttle 134 may simultaneously and independently transport the first carrier 124*a* to/from the first position adjacent the first side 114 of the analyzer 100 and/or the second position adjacent the second side 116.

When a carrier, e.g., the first carrier 124*a*, returns to the first position adjacent the first side 114 of the analyzer 100, the positioner 126 unloads the first carrier 124*a* and places the first carrier 124*a* within one of the slots 122*a-n* in the loading rack 120. The positioner 126 is then able to retrieve the first carrier 124*a* or another carrier 124*b-n* from the loading rack 120 and deposit that carrier 124*a-n* on the first track 144 of the first carrier shuttle 134. By employing two carrier shuttles 134, 136, one of the carrier shuttles 134, 136 can operate to hold a carrier near the second position for aspiration while another carrier can be loaded onto the other carrier shuttle 134, 136 for subsequent transportation to the second side 116 of the analyzer 100. Thus, the time between aspirations is reduced, which increases throughput of the example analyzer 100.

In the example shown, the first and second carrier shuttles 134, 136 are aligned substantially parallel to one another and are disposed along the third side 138 of the analyzer 100. However, in other examples, the first and second carrier shuttles 136, 136 may be positioned other locations and/or not parallel to one another. In the example shown, the first and second carrier shuttles 134, 136 are disposed over a portion of the first carousel 102. In other examples, the first and/or second carrier shuttles 134, 136 are disposed outside of the first carousel 102 (i.e., next to the first carousel 102).

In some examples, test orders are programmed by an operator or downloaded via a lab information system or any network. A test order may require a plurality of assays. Once a sample is loaded, a programmable computer determines the order (e.g., scheduling, protocols) of the different sample tests based on factors including, for example, number of tests to be conducted, types of reagents to be used, number of reagents to be used, an incubation period, scheduled priority and other factors. In the example shown, the positioner 126, the first track 142, the second track 144, the first motor 146, the second motor 148 and other components are controlled in response to commands from the programmable computer.

In the illustrated example shown in FIGS. 1A and 1B, a laboratory automated system (LAS) 154 has a main track 156 and a first subtrack or spur 158, which is disposed along the second side 116 of the analyzer 100. The LAS 154 may include multiple instruments and equipment for processing and preprocessing certain samples, reagents, calibrations, controls, etc. In some examples, the LAS 154 includes and/or is coupled to a refrigerated storage area, a centrifuge, an aliquoter and/or any other processing station(s). In some examples, the LAS includes a system of tracks and robotic positioners to move carriers from one instrument to another.

In the example shown, the LAS 154 transports carriers (e.g., sample carriers) or containers to a position near the analyzer 100 and, more specifically, to a position within the first path of travel 112 of the pipetting mechanism 110. For illustrative purposes, a carrier 124*c* is depicted on the first subtrack or spur 158. In operation, the carrier 124*c* is transported along the main track 156 of the LAS 154 and when the carrier 124*c* arrives at the first spur 158, the carrier 124*c* may continue down the main track 156 or may be diverted to the first spur 158 to be sent to the position adjacent the pipetting mechanism 110. As shown, the path of travel 112 of the pipetting mechanism 110 extends beyond the second side 116 of the analyzer 110. In the example shown, the pipetting mechanism 110 may aspirate a liquid (e.g., a sample) from a container on the carrier at the first spur 158 at point D. In the example shown, the main track 156 and the spur 158 of the LAS 154 are substantially parallel to the second side 116 of the analyzer 100 and are substantially perpendicular to the first and second carrier shuttles 134, 136.

In the example shown, the pipetting mechanism 110 is located near the second side 116 of the analyzer 100 and has access (e.g., can aspirate from and/or can dispense to) to the reaction vessels 108*a-n* on the second carousel 104 at point A, a carrier on the first track 142 of the first carrier shuttle 134 at point B, a carrier on the second track 144 of the second carrier shuttle 136 at point C and/or a carrier on the spur 158 of the LAS 154 at point D. Therefore, the pipetting mechanism 110 has access to carriers loaded in the RSH 118 at the first side 114 (e.g., the front side) of the analyzer 110 (via one or more of the carrier shuttles 134, 136) and carriers transported along the track 156 of the LAS 154 on the second side 116 (e.g., the back side) of the analyzer 100. Continuous access to carriers at different locations around the pipetting mechanism 110 points allows the pipetting mechanism 110 to aspirate from multiple sample containers more efficiently and with less idle or down time and, as a result, increases the throughput of the example analyzer 100.

Figure 2:
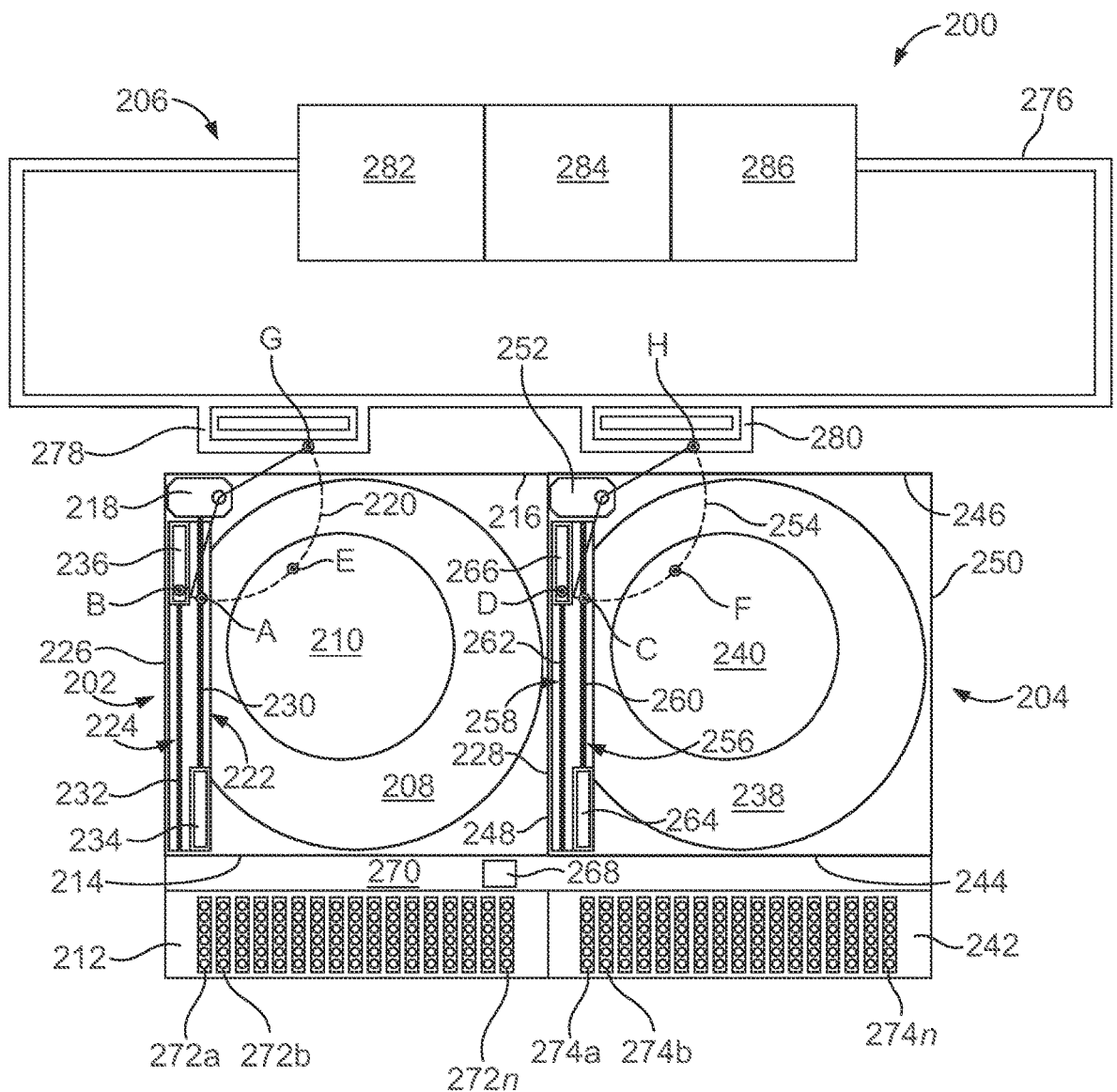
FIG. 2 illustrates an example laboratory system in accordance with the teachings of this disclosure.

FIG. 2 illustrates an example laboratory system 200 having a first diagnostic analyzer 202 (e.g., a first module), a second diagnostic analyzer 204 (e.g., a second module) and a laboratory automation system (LAS) 206. In the example shown, the first analyzer 202 includes a first carousel 208 and a second carousel 210. In the example shown, the second carousel 210 is reaction carousel having a plurality of reaction vessels for conducting diagnostic tests on one or more samples in the plurality of reaction vessels. The first analyzer 202 also includes a first random sample handler (RSH) 212 (e.g., a first loading bay) disposed along a first side 214 (e.g., a front side) of the first analyzer 202, opposite a second side 216 (e.g., a rear side) of the first analyzer 202. A first pipetting mechanism 218 is disposed on the first analyzer 202 adjacent the second side 216 of the first analyzer 202 and has a first path of travel 220 (e.g., horizontal arc path, range of access).

In the example shown, the first analyzer 202 further includes a first carrier shuttle 222 and a second carrier shuttle 224 located along a third side 226 (e.g., the left side) of the first analyzer 202, opposite a fourth side 228 (e.g., the right side) of the first analyzer 202. In the example shown, each of the first and second carrier shuttles 222, 224 has a respective track 230, 232 (e.g., lead screw) and a respective carriage 234, 236 (e.g., shuttles). The first and second tracks 230, 232 operate to move the respective carriages 234, 236 from a first position near the first side 214 of the first analyzer 202 to a second position near the second side 216 of the first analyzer 202 and within the first path of travel 220 of the first pipetting mechanism 218. In the example shown, the first and second carriages 234, 236 are platforms for holding a carrier. As the first and second tracks 230, 232 operate (e.g., rotate), the first and second carriages 234, 236 move along the longitudinal axes of the respective track 230, 232.

In the example shown, the second analyzer 204 includes similar components as the first analyzer 202 such as, for example, a third carousel 238 (e.g., a reagent carousel), a fourth carousel 240 (e.g., a reaction carousel), a second RSH 242, a first side 244 (e.g., a front side) opposite a second side 246 (e.g., a rear side), a third side 248 (e.g., a left side) opposite a fourth side 250 (e.g., a right side), a second pipetting mechanism 252 with a second path of travel 254, a third carrier shuttle 256, a fourth carrier shuttle 258, a third track 260 (e.g., a third lead screw), a fourth track 262 (e.g., a fourth lead screw), a third carriage 264 and a fourth carriage 266. The third and fourth carrier shuttles 256, 258 of the second analyzer 204 operate to transport carriers from a first position adjacent the first side 244 of the second analyzer 204 to a second position adjacent the second side 246 of the second analyzer 204 and within the second path of travel 254 of the second analyzer 204.

In the example shown, a positioner 268 is movable along a positioner path 270 between the first and second RSH 212, 242 and along the first sides 214, 244 of the first and second analyzers 202, 204. In this example, only one positioner 268 is utilized to transport carriers among the first RSH 212, the second RSH 242, the first track 230, the second track 232, the third track 260 and/or the fourth track 262. In some examples, the positioner 268 is substantially similar to the positioner 126 disclosed above in connection with FIGS. 1A and 1B. The positioner 268 may retrieve carriers loaded within the first and second RSH 212, 242 and may transport the carriers via the first, second, third or fourth carrier shuttles 222, 224, 256, 258.

In the example shown, a first plurality of carriers 272a-n are loaded in the first RSH 212, and a second plurality of carriers 274a-n are loaded in the second RSH 242. In operation, the positioner 268 is to retrieve one of the first or second plurality of carriers 272a-n, 274a-n and is to place (e.g., position, deposit, transport) the carrier on one of the first, second, third or fourth carrier shuttles 222, 224, 256, 258. The carriers 272a-n, 274a-n may then be transported via one of the carriages 234, 236, 264, 266 and tracks 230, 232, 260, 262 to a position near the second side 216, 246 of one of the analyzers 202, 204.

In the example shown, the first pipetting mechanism 218 of the first analyzer 202 may aspirate from a container in a first carrier on the first carriage 234 at point A and may aspirate from another container in a second carrier on the second carriage 236 at point B, which are both along the first path of travel 220. Similarly, the second pipetting mechanism 252 may aspirate from a container in a third carrier on the third carriage 264 at point C and may aspirate from another container in a fourth carrier on the fourth carriage 266 at point D, both of which are along the second path of travel 254 of the second pipetting mechanism 252. The first pipetting mechanism 218 may access one or more reaction vessels on the second carousel 210 at point E, and the second pipetting mechanism 252 may access one or more reaction vessels on the fourth carousel 240 at point F.

In the example system shown in FIG. 2, the LAS 206 includes a main track 276 that is disposed along the second sides 216, 246 of the first and second analyzers 202, 204. The main track 276 has a first subtrack or spur 278 and a second subtrack or spur 280. The first spur 278 displaces a carrier on the main track 276 to a position near the second side 216 of the first analyzer 202 and within the first path of travel 220 of the first pipetting mechanism 218. The second spur 280 displaces a carrier on the main track 276 to a position near the second side 246 of the second analyzer 204 and within the second path of travel 254 of the second pipetting mechanism 252. In the example shown, the first pipetting mechanism may aspirate from a container on a carrier on the first spur 278 at point G, and the second pipetting mechanism 252 may aspirate from another container on another carrier on the second spur 280 at point H.

Although only two analyzers 202, 204 are shown in this example, more (e.g, three or four) or fewer analyzers may be added to the laboratory system 200, and the track 276 of the LAS 206 may be configured to traverse along or near the analyzers to supply the analyzers with access to additional carriers. The LAS 206 transports carriers having additional liquids such as, for example, priority samples for testing, calibration and control liquids, additional reagents (including, for example, liquids with microparticles), etc. In some examples, the LAS 206 is tied to additional equipment such as, for example, a refrigerated storage area 282, a centrifuge 284 and/or an aliquoter 286.

In some example tests, such as clinical chemistry tests, a body liquid may be analyzed, such as, for example, serum or plasma. Serum is the yellow, watery part of blood that is left after blood has been allowed to clot and all blood cells have been removed such as, for example, via centrifugation, which packs the denser blood cells and platelets to the bottom of a centrifuge tube and leaves the liquid serum fraction resting above the packed cells. Plasma is similar to serum but is obtained by centrifuging blood without clotting. The LAS 206 of example system 200 enables sample liquids such as, for example, serum or plasma to be processed in the centrifuge 284 and then transported to one or more of the first and second analyzers 202, 204 for diagnostic testing. In other examples, the LAS 206 allows priority samples to be loaded onto carriers and sent along the track 276 to a position within the first and/or second paths of travel 220, 254 of the respective pipetting mechanisms 218, 252. By disposing the pipetting mechanisms 218, 252 near the second sides 216, 246 of the analyzers 202, 204, and by providing the carrier shuttles 222, 224, 256, 258 to transport carrier to and from the first and second sides 214, 244, 216, 246 of the analyzers 202, 204, the analyzers 202, 204 may receive samples in a traditional operating manner through the first sides 214, 244 and/or may receive samples from the LAS 206 at the second sides 216, 246. Additionally, by disposing the pipetting mechanisms 218, 252 near the second sides 216, 246 of the analyzers, the analyzers 202, 204 can be arranged in a side-by-side configuration without interfering with operations of the respective analyzers 202, 204 and, thus, laboratory floor space is decreased.

Figure 3:
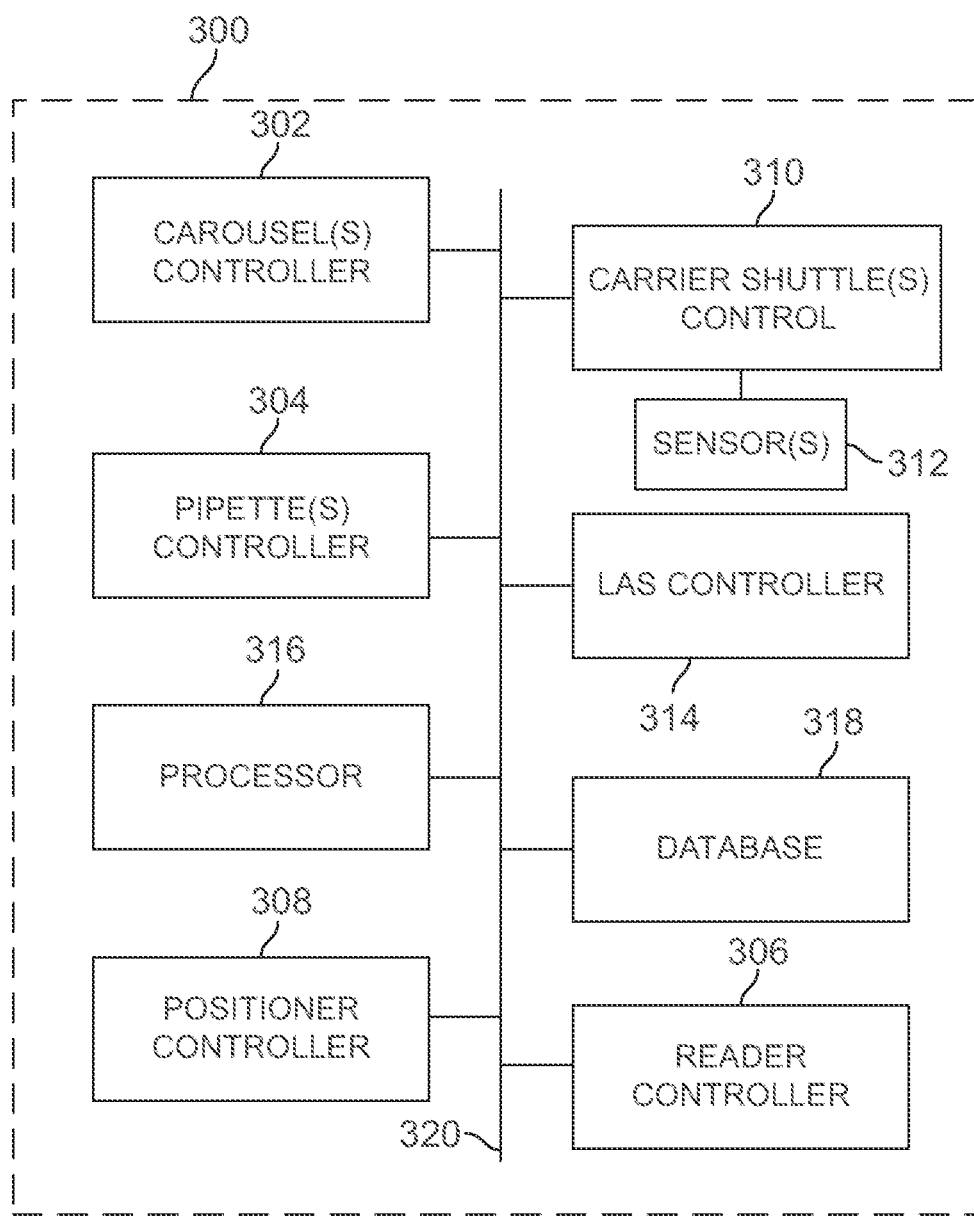
FIG. 3 is a block diagram of an example processing system for the example analyzers and laboratory systems shown in FIGS. 1 and 2.

FIG. 3 is a block diagram of an example processing system 300 for use with any of the analyzers 100, 202, 204 and/or the LAS 154, 206 disclosed herein. Example analyzers disclosed herein are used to, for example, perform diagnostic testing on multiple test samples using one or more reagents and/or other diagnostic test procedures. The example processing system 300 includes a carousel controller 302 to control the operations (e.g., rotational sequences, locksteps, indexing, etc.) of one or more carousels on an analyzer. In some examples, an analyzer includes one or more carousels having a plurality of containers or vessels. In some examples, the analyzer includes a first carousel having a plurality of reagent containers that contain reagents for diagnostic testing and a second carousel having a plurality of vessels (e.g., reaction vessels) that are used for testing the samples. For example, the analyzer 100 disclosed above includes the first carousel 102 (e.g., a reagent carousel), and the second carousel 104 (e.g., a reaction carousel). The second carousel 104 includes a plurality of reaction vessels 108a-n and rotates the reaction vessels 108a-n in a continuous or discrete manner while a plurality of diagnostic functions are performed on the reaction vessels 108-n. The carousel controller 302 may be used, for example, to control the rotational sequence (e.g., lockstep timing) of the first and second carousels 102, 104.

The example processing system 300 includes a pipette controller 304. In some examples, an analyzer utilizes one or more pipettes (e.g., automated pipetting mechanisms, probe arms, etc.) to aspirate a fluid from one location and dispense the fluid into another location. In some examples, an analyzer has multiple pipettes such as, for example, a first pipette for dispensing a sample into a reaction vessel, a second pipette for dispensing a first reagent into a reaction vessel, a third pipette for dispensing a second reagent into a reaction vessel, etc. The pipette controller 306 operates to control the pipettes such as, for example, the movement of the pipettes, the vacuum applied to the pipettes for aspirating, the pressure applied to the pipettes for dispensing, etc. In the example analyzer 100 disclosed above, the analyzer 100 includes the pipetting mechanism 110, which moves a pipette along the path of travel 112 to aspirate and dispense fluid such as, for example, sample. In some examples, the example pipetting mechanism 110 dispenses sample into the reaction vessels 108a-n on the second carousel 104 at point A. The pipette controller 304 is used to control the pipetting mechanism 110.

The example processing system 300 includes a reader controller 306. In some examples, a reader (e.g., an analyzer) is disposed along the inside or the outside of the reaction carousel, such that as the reaction carousel rotates, the reader may analyze the contents of the respective reaction vessels. In some examples, a reaction vessel is held stationary in front of the reader for a predetermined time and a reading is taken. In other examples, one or more reaction vessels may be passed continuously in front of the reader, and the reader takes a plurality of individual readings corresponding to each reaction vessel. The reader controller 306 operates to control when the readings are taken.

The reader controller 306 may also be used to control other readers. For example, a reader positioned near the RSH 118 may be operated to read an RFID tag, a bar code, a QR code or other machine readable code to gather information about the identity of or other data related to the contents of a carrier 124a-n and/or a container coupled to the carrier 124a-n.

The example processing system 300 also includes a positioner controller 308 and a shuttle controller 310. In some examples, an analyzer includes a loading bay for receiving containers, carriers having containers and/or trays of carriers. The containers may include reagents, samples, controls, calibrations, etc. In some examples, the loading bay is disposed on a first side or front side of the analyzer. In some examples, a positioner (e.g., a robotic mechanism) retrieves the carriers from the loading bay and transports the carriers to different areas of the analyzer for testing and retesting. The positioner controller 308 controls the movement of the positioner to engage and move carriers in the analyzer. In the example analyzer 100 disclosed above, the positioner 126 translates along the track 128 on the first side 114 of the analyzer 100. The positioner 126 also has the arm 130 that rotates to engage carriers in the RSH 118. The positioner controller 308 may be used, for example, to control the movement of the positioner 126 and the arm 130 along the track 128.

In some examples, an analyzer includes one or more shuttle carriers to transport carriers from one side of the analyzer to the other side of the analyzer. In some examples, the pipette is disposed along a second side or rear side of the analyzer and the carrier shuttle(s) transports the carriers from the front of the analyzer adjacent the loading bay to a position near the back side of the analyzer and within the range of the pipette. In some examples, the carrier shuttles are operated by motors (e.g., electric motors, servo motors, stepper motors, etc.). In some examples, the shuttle carriers utilize a track system such as, for example, a conveyor belt or a lead screw, to transport the carriers. The carrier shuttle controller 310 operates to control the movement of the one or more carrier shuttles to transport carriers along the carrier shuttle(s). The carrier shuttle controller 310 may be used, for example, to control the motors 146, 148 of the respective carrier shuttles 134, 136.

The example processing system 300 includes sensors 312 communicatively coupled to the shuttle carrier controller 310. In some examples, one or more sensors (e.g., transducers, encoders, etc.) are used to sense movement of the carrier shuttles to determine whether the carrier shuttles are operating in accordance with their instructions from the carrier shuttle controller 310. In some examples, the sensors 312 are disposed at an opposite end of the carrier shuttles than the motors. In the example analyzer 100 disclosed above, the sensors 150, 152 are disposed along the tracks 142, 146 of the respective carrier shuttles 134, 136 to determine whether the tracks 142, 146 of the respective shuttle carriers 134, 136 are operating effectively and that the tracks 142, 146 are not dislodged, misaligned or otherwise inoperable.

The example processing system 300 includes a laboratory automation system (LAS) controller 314. In some examples, a laboratory automation system includes a system of tracks and instruments to transport carriers around a laboratory. Some samples, reagents, and other liquids used in diagnostic testing, require additional processing steps and/or refrigeration. The LAS may connect to various instruments and, when time for processing, the LAS may transport the liquid (e.g., a priority sample), via a carrier, to the back side of the analyzer for aspirating by the pipette. In some examples, the main track of the LAS includes a subtrack or spur to transport a carrier to the rear side of the analyzer, such that the carrier is not held stationary on the main track. The LAS controller 314 controls operation of the LAS including, for example, the main track, the spurs, and/or any equipment or instruments attached thereto. For example, the example LAS 154 disclosed above includes the main track 156 and the spur 158 to transport a carrier (e.g., 124c) to a location adjacent the rear side of the analyzer 100, such that the pipetting mechanism 110 may aspirate from the contents of the carrier.

The example processing system 300 also includes a processor 316 and a database 318. The processor interfaces with the controllers and sensors 302-314 of the processing system 300 to control the various operations of each of the components. The processor 316 is programmable to operate in accordance with desired testing protocol(s). The database 318 may be used to store, for example, information regarding tests that have occurred, are to occur, and/or are occurring, testing protocol(s), information regarding the individual samples and/or reagents data gathered from the reader(s), position(s) of the carrier(s), positioner(s), carrier shuttle(s), pipetting mechanism(s), LAS, and/or carousel(s), and/or other information.

In the example shown, the processing system components 302-318 are communicatively coupled to other components of the example system 300 via communication links 320. The communication links 320 may be any type of wired connection (e.g., a databus, a USB connection, etc.) or a wireless communication mechanism (e.g., radio frequency, infrared, etc.) using any past, present or future communication protocol (e.g., Bluetooth, USB 2.0, USB 3.0, etc.). Also, the components of the example system 300 may be integrated in one device or distributed over two or more devices.

While an example manner of implementing the analyzers 100, 202, 204 and/or the LAS 154, 206 of FIGS. 1A-2 is illustrated in FIG. 3, one or more of the elements, processes and/or devices illustrated in FIG. 3 may be combined, divided, re-arranged, omitted, eliminated and/or implemented in any other way. Further, the example carousel controller 302, the example pipette controller 304, the example reader controller 306, the example positioner controller 308, the example carrier shuttle controller 310, the example sensor(s) 312, the example LAS controller 314, the example processor 316, the example database 318 and/or, more generally, the example processing system 300 of FIG. 3 may be implemented by hardware, software, firmware and/or any combination of hardware, software and/or firmware. Thus, for example, any of the example carousel controller 302, the example pipette controller 304, the example reader controller 306, the example positioner controller 308, the example carrier shuttle controller 310, the example sensor(s) 312, the example LAS controller 314, the example processor 316, the example database 318 and/or, more generally, the example processing system 300 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example carousel controller 302, the example pipette controller 304, the example reader controller 306, the example positioner controller 308, the example carrier shuttle controller 310, the example sensor(s) 312, the example LAS controller 314, the example processor 316 and/or the example database 318 is/are hereby expressly defined to include a tangible computer readable storage device or storage disk such as a memory, a digital versatile disk (DVD), a compact disk (CD), a Blu-ray disk, etc. storing the software and/or firmware. Further still, the example processing system 300 of FIG. 3 may include one or more elements, processes and/or devices in addition to, or instead of, those illustrated in FIG. 3, and/or may include more than one of any or all of the illustrated elements, processes and devices.

Figure 4:
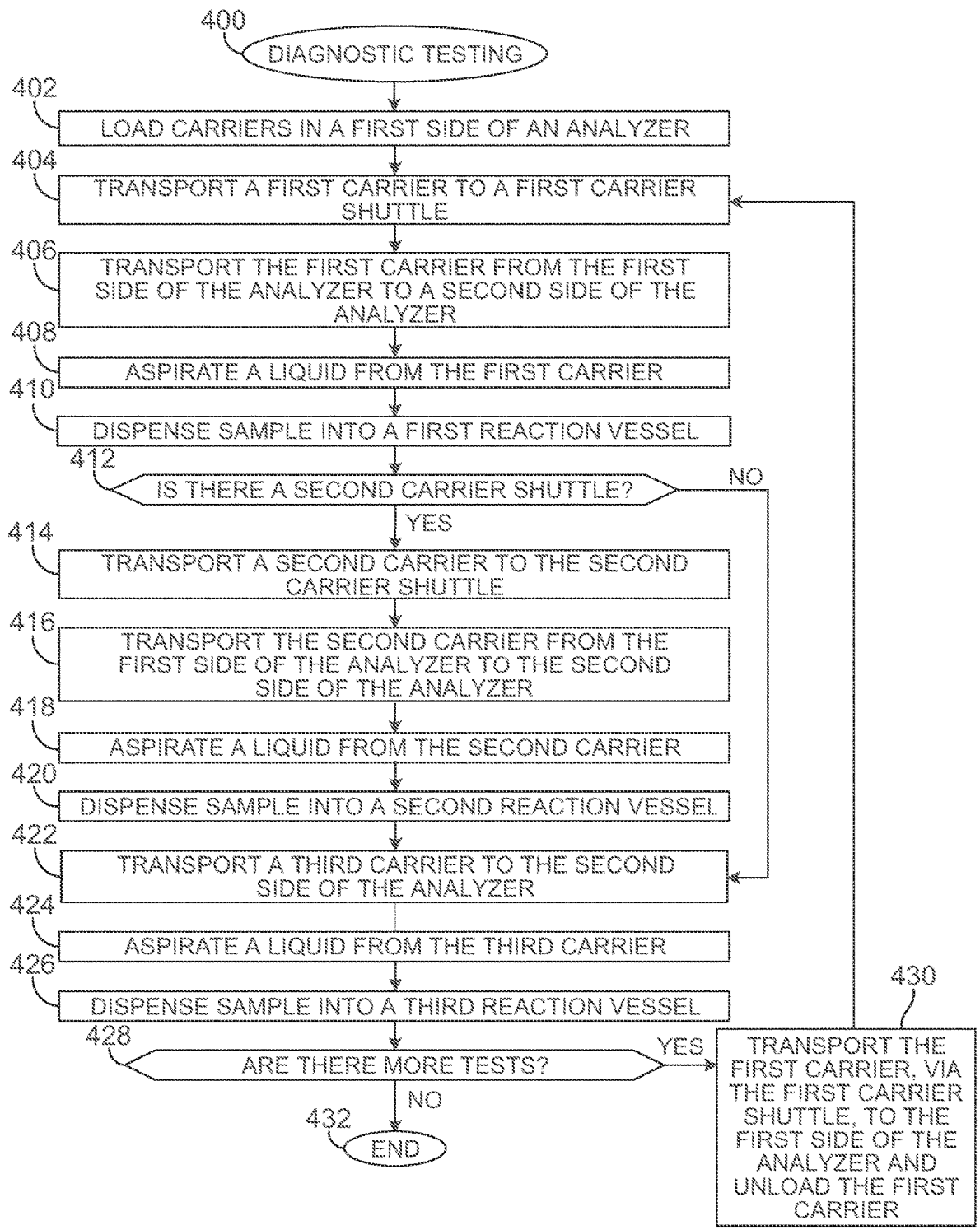
FIG. 4 is a flowchart illustrating an example diagnostic testing process.

A flowchart representative of an example method 400, at least some of which are machine readable, for implementing the example analyzers 100, 202, 204, the example LAS 154, 206 and/or the example processing system 300 is shown in FIG. 4. In this example, the method 400 may be implemented using machine readable instructions that comprise a program for execution by a processor such as the processor 512 shown in the example processor platform 500 discussed below in connection with FIG. 5. The program may be embodied in software stored on a tangible computer readable storage medium such as a CD-ROM, a floppy disk, a hard drive, a digital versatile disk (DVD), a Blu-ray disk, or a memory associated with the processor 512, but the entire program and/or parts thereof could alternatively be executed by a device other than the processor 512 and/or embodied in firmware or dedicated hardware. Further, although the example program is described with reference to the flowchart illustrated in FIG. 4, many other methods of implementing the example analyzers 100, 202, 204, the example LAS 154, 206 and/or the example processing system 300 may alternatively be used. For example, the order of execution of the blocks may be changed, and/or some of the blocks described may be changed, eliminated, or combined.

As mentioned above, at least some of the elements of the process of FIG. 4 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals. As used herein, "tangible computer readable storage medium" and "tangible machine readable storage medium" are used interchangeably. Additionally or alternatively, the example processes of FIG. 4 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable device or disk and to exclude propagating signals. As used herein, when the phrase "at least" is used as the transition term in a preamble of a claim, it is open-ended in the same manner as the term "comprising" is open ended.

FIG. 4 is a flowchart representing the example diagnostic testing method 400 that may be implemented, for example, by the analyzers 100, 202, 204, the LAS 154, 206 and/or the processing system 300 detailed above. The example analyzers include a first carousel and a second carousel, the second carousel being a reaction carousel having a plurality of reaction vessels for conducting diagnostic tests. As the reaction carousel rotates, a plurality of automated modules each perform assay steps on the individual reaction vessels. The example analyzers have a first side (e.g., a front side) and a second side (e.g., a back side), opposite the first side. In the example analyzers 100, 202, 204 detailed above, a pipetting mechanism is disposed near the second side of the analyzer to dispense sample into the reaction vessels on the reaction carousel as the reaction carousel rotates. In some examples, a loading bay is disposed on the first side of the example analyzer to receive carriers or trays of carriers. The example method or process 400 includes loading carriers in the first side of the analyzer (block 402). In some examples, each carrier includes multiple containers such as, for example, test tubes having test samples.

The example process 400 also includes transporting a first carrier to a first carrier shuttle (block 404). For example, the example analyzer 100 disclosed above includes a first carrier shuttle 134 and a second carrier shuttle 136 to transport carriers from the first side 114 of the analyzer 100 to the second side 116 of the analyzer 100. In some examples, a positioner is located along the loading bay to retrieve carriers from respective slots and transfer the carriers to other locations in the analyzer including, for example, to a carrier shuttle.

The example process 400 includes transporting the first carrier from the first side of the analyzer to the second side of the analyzer (block 406). In some examples, the first carrier shuttle includes a conveyor belt and a motor to transport the first carrier. In other examples, the first carrier shuttle comprises a lead screw and a carriage, such that the first carrier may be placed in the carriage and the first lead screw operates (e.g., rotates) to move the carriage (and the first carrier) from the first side of the analyzer to the second side of the analyzer. In some examples, the first carrier shuttle has a sensor (e.g., an encoder, a transducer) to sense movement of the conveyor belt, as a safety feature.

The example process 400 also includes aspirating a liquid from the first carrier (block 408). For example, the example analyzer 100 disclosed above locates the pipetting mechanism 110 adjacent the second side 116 of the analyzer 100. The first carrier shuttle 134 is to transport the first carrier from a first location near the first side 114 of the analyzer 100 to a second location near the second side 116 of the analyzer and, more specifically, within an access range (e.g., the path of travel 112, a horizontal arc path, etc.) of the pipetting mechanism 110, to enable the pipetting mechanism 110 to aspirate from the first carrier. After aspiration, the liquid is dispensed into a first reaction vessel (block 410). In some examples, the pipetting mechanism 110 has an axis of rotation and a probe arm with a pipette disposed on the distal end of the probe arm. The probe arm rotates to access liquids along a path of travel (e.g., a horizontal arc path) and dispenses the aspirated liquid into the first reaction vessel on the reaction carousel 104.

The example process includes determining whether there is a second carrier shuttle (412). In some examples, the analyzer employs only one carrier shuttle. In the example analyzers 100, 202, 204 disclosed above, a second carrier shuttle is utilized to reduce turnaround time and increase throughput. The second carrier shuttle is independently operated. Therefore, one or more of the operations of the second carrier shuttle and/or components related thereto (e.g., blocks 314, 316, 318, 320) may occur independently and/or simultaneously relative to the one or more of the operation of the first carrier shuttle and/or components related thereto (e.g., blocks 304, 306, 308, 310).

The example process 400 includes transporting a second carrier to the second carrier shuttle (block 414). For example, as mentioned above, the positioner 126 of the analyzer 100 retrieves the second carrier 124b-n from a slot 122b-n in the loading bay 120 and transports the second carrier 124b-n to the second carrier shuttle 136.

The example process 400 also includes transporting the second carrier from the first side of the analyzer to the second side of the analyzer (block 416). In some examples, the second carrier shuttle includes a conveyor belt or a lead screw. The second carrier shuttle operates to transport the second carrier from the first location near the first side of the analyzer to the second location adjacent the second side of the analyzer and, more specifically, to a location within the path of travel of the pipetting mechanism.

The example process 400 includes aspirating a liquid from the second carrier (block 418) and dispensing the liquid into a second reaction vessel on the reaction carousel (420).

In addition, the example process 400 includes transporting a third carrier to the second side of the analyzer (block 422). For example, the example analyzer 100 may include the laboratory automation system (LAS) 154. The LAS 154 has a track system 156 to transport carriers and/or containers of diagnostic testing liquid around a laboratory, and a portion of the track (e.g., 158) is disposed adjacent the second side of the analyzer. The transport of the third carrier is independent of the transport of the first and/or second carriers. Therefore, one or more of the operations of the first and second carrier shuttle and/or components related thereto (e.g., blocks 304, 308, 310, 312, 314, 316, 318, 320) may occur independently and/or simultaneously relative to the one or more of the operation of the LAS 154 and/or components related thereto (e.g., blocks 322, 324, 326).

The example process 400 also includes aspirating a liquid from the third carrier (block 424). For example, the LAS 154 includes the spur 158 that directs the third carrier 124c from the main track 156 to a position within the path of travel 112 of the pipetting mechanism 110 to enable access for aspirating the liquid from the third carrier 124c. The example process 300 also includes dispensing the liquid into a third reaction vessel on the reaction carousel (block 426). For example, the pipetting mechanism 110 may move in the path of travel 112 and dispense aspirated liquid into a reaction vessel on the second carousel 104.

The example process includes determining whether additional tests are to be performed (block 428). If further testing is desired, then the example process includes transporting the first carrier, via the first shuttle carrier, from the second location to the first location adjacent the first side of the analyzer (block 430). In some examples, the positioner removes the first carrier from the first carrier shuttle and places the first carrier in an empty slot in the loading bay. The example process may then continue with loading or transporting another carrier (block 404) onto the first carrier shuttle (i.e., as the "first" carrier in the illustrated example process 400), and the example process 400 proceeds as disclosed above. If further testing is not desired and/or needed (bock 428), then the example process 400 ends (block 432).

Figure 5:
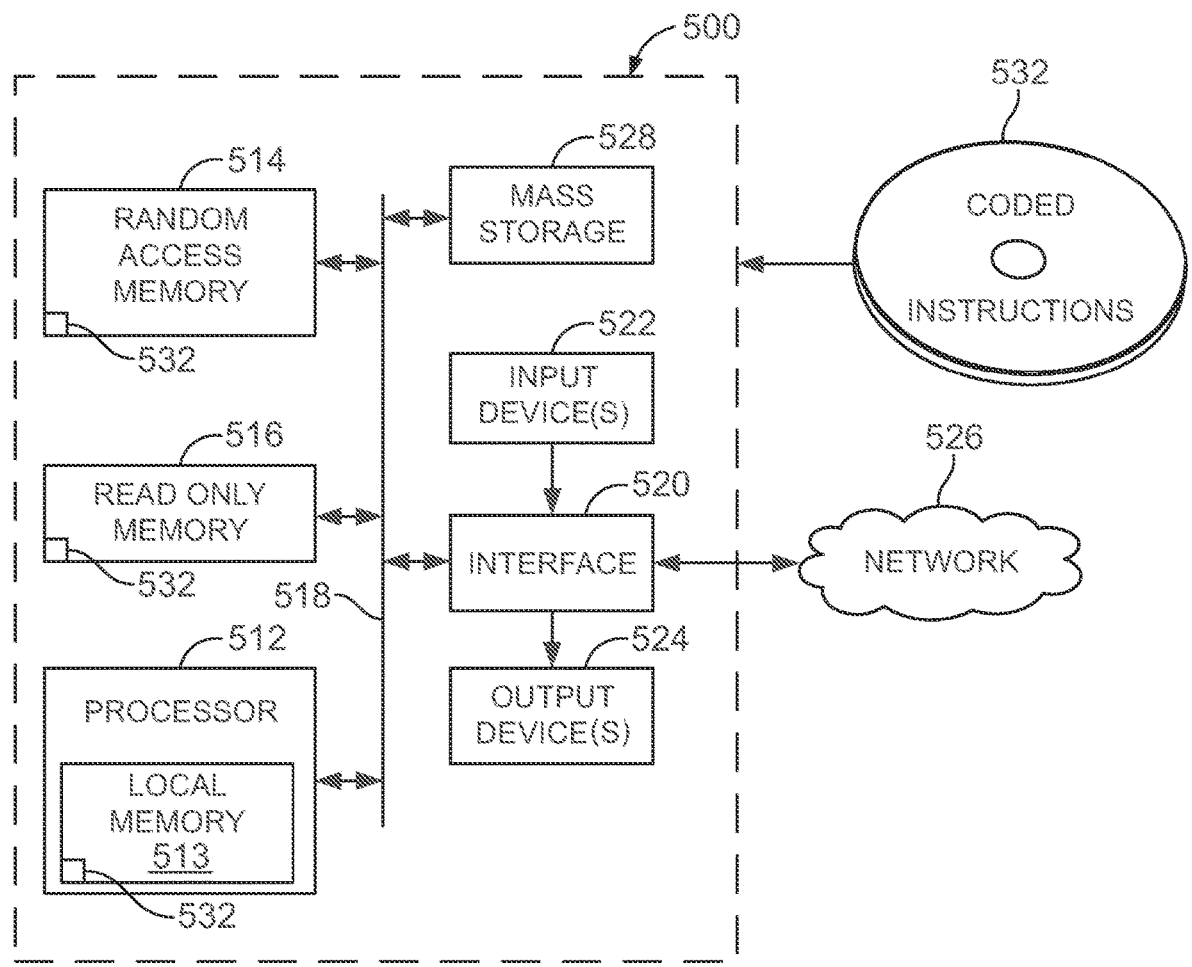
FIG. 5 is a diagram of a processor platform for use with the examples disclosed herein.

FIG. 5 is a block diagram of an example processor platform 500 capable of executing the instructions to be performed of FIG. 4 to implement one or more portions of the apparatus and/or systems of FIGS. 1A-3. The processor platform 500 can be, for example, a server, a personal computer, a mobile device, a personal digital assistant (PDA), an Internet appliance, and/or or any other type of computing device.

The processor platform 500 of the illustrated example includes a processor 512. The processor 512 of the illustrated example is hardware. For example, the processor 512 can be implemented by one or more integrated circuits, logic circuits, microprocessors or controllers from any desired family or manufacturer.

The processor 512 of the illustrated example includes a local memory 513 (e.g., a cache). The processor 512 of the illustrated example is in communication with a main memory including a volatile memory 514 and a non-volatile memory 516 via a bus 518. The volatile memory 514 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 516 may be implemented by flash memory and/or any other desired type of memory device. Access to the main memory 514, 516 is controlled by a memory controller.

The processor platform 500 of the illustrated example also includes an interface circuit 520. The interface circuit 520 may be implemented by any type of interface standard, such as an Ethernet interface, a universal serial bus (USB), and/or a PCI express interface.

In the illustrated example, one or more input devices 522 are connected to the interface circuit 520. The input device(s) 522 permit(s) a user to enter data and commands into the processor 512. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 524 are also connected to the interface circuit 520 of the illustrated example. The output devices 524 can be implemented, for example, by display devices (e.g., a light emitting diode (LED), an organic light emitting diode (OLED), a liquid crystal display, a cathode ray tube display (CRT), a touchscreen, a tactile output device and/or a light emitting diode (LED). The interface circuit 520 of the illustrated example, thus, typically includes a graphics driver card, a graphics driver chip or a graphics driver processor.

The interface circuit 520 of the illustrated example also includes a communication device such as a transmitter, a receiver, a transceiver, a modem and/or network interface card to facilitate exchange of data with external machines (e.g., computing devices of any kind) via a network 526 (e.g., an Ethernet connection, a digital subscriber line (DSL), a telephone line, coaxial cable, a cellular telephone system, etc.).

The processor platform 500 of the illustrated example also includes one or more mass storage devices 528 for storing software and/or data. Examples of such mass storage devices 528 include floppy disk drives, hard drive disks, compact disk drives, Blu-ray disk drives, RAID systems, and digital versatile disk (DVD) drives.

Coded instructions 532 to implement the method of FIG. 4 may be stored in the mass storage device 528, in the volatile memory 514, in the non-volatile memory 516, and/or on a removable tangible computer readable storage medium such as a CD or DVD.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A diagnostic analyzer comprising:
    a base having a first side and a second side opposite the first side;
    a loading bay disposed along the first side of the base;
    a first carrier shuttle on the base, the first carrier shuttle having a first end at a first area adjacent the loading bay and a second end, opposite the first end, at a second area adjacent the second side of the base, the first carrier shuttle to transport a first carrier between the first area and the second area;
    a second carrier shuttle on the base, the second carrier shuttle disposed adjacent the first carrier shuttle, the first and second carrier shuttles being independently operable, the second carrier shuttle having a third end at the first area adjacent the loading bay and fourth second end, opposite the third end, at the second area adjacent the second side of the base, the second carrier shuttle to transport a second carrier between the first area and the second area; and
    a pipetting mechanism coupled to the base and disposed adjacent the second side of the base, the pipetting mechanism to:
        aspirate a first sample from the first carrier while the first carrier is on the first carrier shuttle at the second area;
        dispense the first sample into a first reaction vessel;
        aspirate a second sample from the second carrier while the second carrier is on the second carrier shuttle at the second area; and
        dispense the second sample into a second reaction vessel.

2. The diagnostic analyzer of claim 1, wherein the first carrier shuttle and the second carrier shuttle are parallel to each other.

3. The diagnostic analyzer of claim 1, further including a positioner to transport the first carrier between the loading bay and the first carrier shuttle, and to transport the second carrier between the loading bay and the second carrier shuttle.

4. The diagnostic analyzer of claim 3, wherein the positioner is moveable along a track disposed along the first side of the base, between the base and the loading bay.

5. The diagnostic analyzer of claim 4, wherein the track is perpendicular to the first and second carrier shuttles.

6. The diagnostic analyzer of claim 1, wherein the first carrier shuttle includes a first carriage and a first lead screw to move the first carriage, and the second carrier shuttle includes a second carriage and a second lead screw to move the second carriage.

7. The diagnostic analyzer of claim 1, wherein the first carrier shuttle includes a first conveyor belt and the second carrier shuttle includes a second conveyor belt.

8. The diagnostic analyzer of claim 7, wherein the first carrier shuttle includes a motor to move the first conveyor belt and a sensor to detect movement of the first conveyor belt.

9. The diagnostic analyzer of claim 8, wherein the motor and the sensor are disposed near opposite ends of the first carrier shuttle.

10. The diagnostic analyzer of claim 1, further including a processing carousel on the base, the first and second reaction vessels disposed on the processing carousel, and wherein the first and second carrier shuttles are disposed between the processing carousel and a third side of the base.

11. At least one machine readable storage medium comprising instructions that, when executed, cause at least one processor of a diagnostic analyzer to at least:
    control a first carrier shuttle to transport a first carrier from a first area adjacent a first side of a base of the diagnostic analyzer to a second area adjacent a second side of the base, the first carrier shuttle having a first end at the first area and a second end, opposite the first end, at the second area, the second side of the base opposite the first side of the base, the diagnostic analyzer having a loading bay disposed along the first side of the base;
    control a pipetting mechanism coupled to the base adjacent the second side to:
        aspirate a first sample from the first carrier while the first carrier is at the second area; and
        dispense the first sample into a first vessel on the diagnostic analyzer;

control a second carrier shuttle disposed adjacent the first carrier shuttle to transport a second carrier from the first area to the second area, the second carrier shuttle having a third end at the first area and a fourth end, opposite the third end, at the second area; and control the pipetting mechanism to:
aspirate a second sample from the second carrier while the second carrier is at the second area; and
dispense the second sample into a second vessel on the diagnostic analyzer.

12. The at least one machine readable storage medium of claim 11, wherein the diagnostic analyzer includes a positioner moveable along the first side of the base, and wherein the instructions, when executed, cause the at least one processor to control the positioner to transport the first carrier from a slot in the loading bay to the first carrier shuttle.

13. The at least one machine readable storage medium of claim 12, wherein the instructions, when executed, cause the at least one processor to:
after the first sample is aspirated, control the first carrier shuttle to transport the first carrier from the second area to the first area; and
control the positioner to transfer the first carrier from the first carrier shuttle to a slot in the loading bay.

14. The at least one machine readable storage medium of claim 12, wherein the positioner includes a label reader, and wherein the instructions, when executed, cause the at least one processor to control the label reader to read a label on the first carrier.

15. The at least one machine readable storage medium of claim 11, wherein the first vessel and the second vessel are to be carried on a carousel of the diagnostic analyzer, and wherein the instructions, when executed, cause the at least one processor to control the carousel to rotate the carousel to move reaction vessels.

16. The diagnostic analyzer of claim 3, wherein the positioner includes a reader to detect labels on the first and second carriers.

17. The diagnostic analyzer of claim 10, wherein the pipetting mechanism is rotatable about an axis disposed outside of the processing carousel.

18. The diagnostic analyzer of claim 1, wherein the pipetting mechanism includes an arm that is rotatable about an axis of rotation and a pipette at a distal end of the arm.

19. The diagnostic analyzer of claim 1, wherein the loading bay includes a plurality of slots arranged in a horizontal array along the first side of the base.

20. The diagnostic analyzer of claim 1, further including a first carousel to support a plurality of reagent containers and a second carousel to support a plurality of reaction vessels.

21. A diagnostic analyzer comprising:
a base having a first side and a second side opposite the first side;
a loading bay disposed along the first side of the base;
a first carrier shuttle on the base, the first carrier shuttle extending in a linear direction that is perpendicular to the first side and the second side, the first carrier shuttle to transport a first carrier from a first area adjacent the loading bay to a second area adjacent the second side of the base;
a second carrier shuttle on the base, the second carrier shuttle disposed adjacent the first carrier shuttle, the first and second carrier shuttles being independently operable, the second carrier shuttle extending in a linear direction that is perpendicular to the first side and the second side, the second carrier shuttle to transport a second carrier from the first area adjacent the loading bay to the second area adjacent the second side of the base; and
a pipetting mechanism coupled to the base and disposed adjacent the second side of the base, the pipetting mechanism to:
aspirate a first sample from the first carrier while the first carrier is on the first carrier shuttle at the second area;
dispense the first sample into a first reaction vessel;
aspirate a second sample from the second carrier while the second carrier is on the second carrier shuttle at the second area; and
dispense the second sample into a second reaction vessel.

* * * * *